US010519427B2

(12) United States Patent
Lawrence et al.

(10) Patent No.: US 10,519,427 B2
(45) **Date of Patent: *Dec. 31, 2019**

(54) METHOD FOR PORCINE CIRCOVIRUS PRODUCTION AND PCV2 VACCINES

(71) Applicant: BOEHRINGER INGELHEIM ANIMAL HEALTH USA INC., Duluth, GA (US)

(72) Inventors: Paulraj Lawrence, Arden Hills, MN (US); Frederic Dumas, Athens, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/914,420

(22) Filed: Mar. 7, 2018

(65) Prior Publication Data

US 2018/0201906 A1 Jul. 19, 2018

Related U.S. Application Data

(63) Continuation of application No. 15/154,028, filed on May 13, 2016, now Pat. No. 9,944,904.

(60) Provisional application No. 62/161,457, filed on May 14, 2015.

(51) Int. Cl.

| | |
|---|---|
| ***C12N 7/00*** | (2006.01) |
| ***A61K 39/12*** | (2006.01) |
| ***A61K 39/00*** | (2006.01) |

(52) U.S. Cl.

CPC ................ *C12N 7/00* (2013.01); *A61K 39/12* (2013.01); *A61K 2039/5252* (2013.01); *A61K 2039/552* (2013.01); *C12N 2750/10034* (2013.01); *C12N 2750/10051* (2013.01)

(58) Field of Classification Search

None

See application file for complete search history.

(56) References Cited

U.S. PATENT DOCUMENTS

| | | | | |
|---|---|---|---|---|
| 6,368,601 | B1 | 4/2002 | Allen | |
| 7,144,698 | B2 | 12/2006 | Wang | |
| 7,192,594 | B2 | 3/2007 | Haines | |
| 7,504,206 | B2 | 3/2009 | Haines | |
| 7,741,039 | B2 | 6/2010 | Wang | |
| 9,944,904 | B2 * | 4/2018 | Lawrence | A61K 39/12 |
| 2008/0305128 | A1 | 12/2008 | Fachinger | |
| 2009/0017064 | A1 | 1/2009 | Wu | |
| 2011/0008871 | A1 | 1/2011 | Lau | |
| 2011/0189227 | A1 | 8/2011 | Song | |
| 2012/0164170 | A1 | 6/2012 | Kuo | |
| 2016/0333322 | A1 | 11/2016 | Lawrence | |
| 2018/0201906 | A1 * | 7/2018 | Lawrence | A61K 39/12 |

FOREIGN PATENT DOCUMENTS

| | | |
|---|---|---|
| CN | 103100082 | 5/2013 |
| WO | WO1999018214 | 4/1999 |
| WO | WO9945956 | 9/1999 |
| WO | WO2002077210 | 10/2002 |
| WO | WO2015051099 | 4/2015 |

OTHER PUBLICATIONS

Allan et al., 1998, "Isolation of porcine circovirus-like viruses from pigs with a wasting disease in the US and Europe", J. Vet. Diagn. Invest. 10 (1), 3-10.
Allan et al., 2000, "Porcine circoviruses: a review", J. Vet. Diagn. Investigation 12:3-14.
Allan G., 1995, "Pathogenesis of porcine circovirus; experimental infections of colostrum deprived piglets and examination of pig foetal material", Vet. Microbiol 44: 49-64.
Cino-Ozuna et al., 2011, "Characterization of a new disease syndrome assocaited with porcine circovirus type 2 in previously vaccianted herds", J. Clin. Microbiol. 49 (5), 2012-2016.
Dupont et al., 2008, "Genomic analysis of PCV2 isolates from Danish archives and a current PMWS case-control study supports a shift in genotypes with time", Vet Microbiol. 128 (1-2), 56-64.
GenBank Accession No. AF055392.
Harding et al., 1998, "Postweaning multisystemic wasting syndrome: epidemiology and clinical presentation", J. Swine Health Prod. 6, 249-254.
Horlen et al., 2008, "A field evaluation of mortaility rate and growth performance in pigs vaccinated against porcine circovirus type 2", J. Am. Vet. Med. Assoc. 232 (6), 906-912.
Kekarainen, 2014, "Genetic variability of porcine circovirus 2 in vacccinating and non-vaccinating commercial farms", J. General Virology, 95, 1734-1742).
Krakowka et al., 2008, "Evaulation of induction of porcine dermatitis and nephropathy syndrome in gnotobiotic pigs with negative results for porcine circovirus type 2", Am. J. Vet. Res. 69, 1615-1622.
Meehan et al., 1997, "Sequence of porcine circovirus DNA: affinities with plant circoviruses", J Gen Vir. vol. 78, pp. 221-227.
Meehan et al., 1998, "characterization of novel circovirus DNAs assocaited with wasting syndromese in pigs", Journal of General Virology 79(9):2171-2719.
Opriessnig et al., 2007, "Porcine circovirus type 2-assocaited disease: update on current terminology, clinical manifestations, pathogenesis, diagnosis, and intervention strategies", J. Vet. Diagn. Invest. 19 (6), 591-615.
Rose et al.,2012, "epidemiology and transmission of porcine circovirus type 2 (PCV2)", Virus Research, 164, 78-89.

(Continued)

*Primary Examiner* — Shanon A. Foley

(74) *Attorney, Agent, or Firm* — Judy Jarecki-Black; Steffan Finnegan

(57) ABSTRACT

This invention relates to a method for rapid production of PCV2 such that an optimum yield of the virus can be obtained. This invention also relates to the vaccine useful against PCV2 which includes the PCV2 propagated using such a method.

12 Claims, 12 Drawing Sheets

Specification includes a Sequence Listing.

(56) References Cited

OTHER PUBLICATIONS

Segalés et al., 1997, "First report of post-weaning multisystemic wasting syndrome in pigs in Spain", Vet. Rec. 141, 600-601.
Segalés et al., 2008, "PCV-2 genotype definition and nomenclature", Vet. Rec. 162 (26), 867-868.
Thomson et al., 2002, "Porcine dermatitis and nephropathy syndrome. Clinical and pathological features of cases in the United Kingdom (1993-1998)", J. Vet. Med. A: Physiol. Pathol. Clin. Med. 49, 430-437.
Tischer et al., 1982, "A very small porcine cirus with circular single-stranded DNA", Nature 295:64-66.
Tischer et al., 1986, "Studies on epideminology and pathogenicity of porcine circovirus", Arch. Virol 91:271-276.
Tischer et al., 1987, "Replication of procine circovirus induction by glucosamine and cell cycle dependence", Arch Virol. 96:39-57.
Wellenberg et al., 2004, "Excessive procine circovirus type 2 antibody titres may trigger the developmenet of porcine dermatitis and nephropathy syndrome: a case-control study", Vet. Microbiol. 99 (3-4), 203-214.
Chen et al., 2013, "Highly permissive subclone of the porcine kidney cell line for porcine circovirus type 2 production", J. of Virological Methods 187: 380-383.
Fort et al., 2008, "Porcine circovirus type 2 (PCV2) vaccination of conventional pigs prevents viremia against PCV2 isolates of different genotypes and geographic origins", Vaccine, 26:1063-1071.
Hull et al., 1976, "The origin and characteristics of a pig kidney cell strain, LLC-PK1", In Vitro, 12(10): 670-677.
Baumann et al., 2013, "Porcine circovirus type 2 stimulates plasmacytoid dendritic cells in the presence of IFN-gamma", Veterinary Immunology and immunopathology, 156: 223-228.
Cheung et al., 2007, "Detection of two porcine circovirus type 2 genotypic groups in United States swine herds", Archives of Virology, 152: 1035-1044.
Cai et al., 2012, "Identification of an emerging recombinant cluster in porcine circovirus type 2", Virus Research 165: 95-102.

* cited by examiner

Current PCV2 production process

Chart showing the relationship between live titer before inactivation and the resulting ELISA titer after inactivation for the AI produced ELISA titer function of the percentage of seed used for inoculation The size of the bubbles represents the MOI (ratio between the number of virus particle and the number of cells to be infected)

Live titer evolution over seed amplification

Persistently infected cell line process flow chart

VSR function of the percentage of seed percentage per volume of culture

The size of the bubble is proportional to the live titer of the seed

Figure 7

| SEQ ID NO: | Type | Gene description |
|---|---|---|
| 1 | DNA | DNA sequence of PCV2 isolate 12-1761-1 |
| 2 | protein | Protein sequence of PCV2 isolate 12-1761-1 |
| 3 | DNA | DNA sequence of PCV2 isolate 12-1758-1 |
| 4 | protein | Protein sequence of PCV2 isolate 12-1758-1 |
| 5 | DNA | DNA sequence of PCV2 isolate 12-1759-1 |
| 6 | protein | Protein sequence of PCV2 isolate 12-1759-1 |

Figure 8A

DNA sequence alignment

```
                   1                                                50
12-1758-1    (1)   GGCCAAATCCTCCGCCGCCGCCCCTGGCTCGTGCACCCCCGCCACCGCTA
12-1759-1    (1)   GGCCAGATCCTCCGCCGCCGCCCCTGGCTCGTTCACCCCCGCCACCGCTA
12-1761-1    (1)   GGCCAGATCCTCCGCCGCCGCCCCTGGCTCGTGCACCCCCGCCACCGTTA

                   51                                              100
12-1758-1   (51)   CCGATGGAGAAGGAAAAATGGCATCTTCAACACCCGCCTGTCCCGCACCT
12-1759-1   (51)   CCGTTGGAGAAGGAAAAATGGCATCTTCAACACCCGCCTGTCCCGCACCT
12-1761-1   (51)   CCGCTGGGTAAGGAAAAATGGCATCTTCAACACCCGCCTATCCCGCACCT

                   101                                             150
12-1758-1  (101)   TCGGATATACTGTCAAGTTTACCACAGTCAGAACGCCCTCCTGGCGGTG
12-1759-1  (101)   TCGGATATACTGTCAAGTTTACCACAGTCAGAACGCCCTCCTGGCGGTG
12-1761-1  (101)   TCGGATATACTATCAAGCGAACCACAGTCAGAACGCCCTCCTGGCGGTG

                   151                                             200
12-1758-1  (151)   GACATGATGAGATTTAATCTTGAGGACTTTGTTCCCCCGGGAGGGGGGAC
12-1759-1  (151)   GACATGATGAGATTTAATCTTGAGGACTTTGTTCCCCCGGGAGGGGGGAC
12-1761-1  (151)   GACATGATGAGATTCAATATTAATGACTTTCTTCCCCCAGGAGGGGGCTC

                   201                                             250
12-1758-1  (201)   CAACAAAATCTCTATACCCTTTGAATACTACAGAATAAGAAAAGTTAAGG
12-1759-1  (201)   CAACAAAATCTCTATACCCTTTGAATACTACAGAATAAGAAAAGTTAAGG
12-1761-1  (201)   AAACCCCCGCTCTGTGCCCTTTGAATACTACAGAATAAGAAAGGTTAAGG

                   251                                             300
12-1758-1  (251)   TTGAATTCTGGCCCTGCTCCCCAATCACCCAGGGTGATAGGGGAGTGGC
12-1759-1  (251)   TTGAATTCTGGCCCTGCTCCCCAATCACCCAGGGTGATAGGGGAGTGGC
12-1761-1  (251)   TTGAATTCTGGCCCTGCTCCCCGATCACCCAGGGTGACAGGGGAGTGGC

                   301                                             350
12-1758-1  (301)   TCCAATGCTGTTATTCTAGATGATAACTTTGTAGCAAAGGTCATGGCCCA
12-1759-1  (301)   TCCAATGCTGTTATTCTAGATGATAACTTTGTAGCAAAGGTCATGGCCCA
12-1761-1  (301)   TCCAGTGCTGTTATTCTAGATGATAACTTTGTAACAAAGGCCACAGCCCT

                   351                                             400
12-1758-1  (351)   AACCTATGACCCATATGTAAACTACTCCTCCCGCCATACAATGGCCCAAC
12-1759-1  (351)   AACCTATGACCCATATGTAAACTACTCCTCCCGCCATACAATGGCCCAAC
12-1761-1  (351)   CACCTATGACCCCTATGTAAACTACTCCTCCCGCCATACCATAACCCAGC

                   401                                             450
12-1758-1  (401)   CCTTCTCGTACCACTCCCGTTACTTCACACCCAAACCTGTTCCTTGAGTCC
12-1759-1  (401)   CCTTCTCATACCACTCCCGTTACTTCACACCCAAACCTGTTCCTTGAGTCC
12-1761-1  (401)   CCTTCTCATACCACTCCCGCTACTTCACCCCCAAACCTATCCTAGATTCC

                   451                                             500
12-1758-1  (451)   ACTATTGATTACTTCCAACCAAATAACAAAAGGAATCAGCTTTGGCTGAG
12-1759-1  (451)   ACTATTGATTACTTCCAACCAAATAACAAAAGGAATCAGCTTTGGCTGAG
12-1761-1  (451)   ACTATTGATTACTTCCAACCAAACAACAAAAGAAACCAGCTGTGGCTAAG
```

Figure 8B

```
                501                                                550
12-1758-1  (501) GCTACAAACCACTAGAAATGTGGACCACGTAGGCCTCGGCACTGCGTTCG
12-1759-1  (501) GCTACAAACCACTAGAAATGTGGACCACGTAGGCCTCGGCACTGCGTTCG
12-1761-1  (501) ACTACAAACTGCTGGAAATGTAGACCACGTAGGCCTCGGCACTGCATTCG

                551                                                600
12-1758-1  (551) AAAACAGTATATACGACCAGGAGTACAATATCCGTGTAACCATGTATGTA
12-1759-1  (551) AAAACAGTATATACGACCAGGAGTACAATATCCGTGTAACCATGTATGTA
12-1761-1  (551) AAAACAGTATATACGACCAGGAATACAATATCCGTGTAACCATGTATGTA

                601                                           645
12-1758-1  (601) CAATTCAGAGAATTTAATCTTAAAGACCCCCCACTTAAACCGTAA
12-1759-1  (601) CAATTCAGAGAATTTAATCTTAAAGACCCCCCACTTAAACCGTAA
12-1761-1  (601) CAATTCAGAGAATTTAATCTTAAAGACCCCCCACTTAACCCTTAA

12-1761-1 DNA:   SEQ ID NO:1
12-1758-1 DNA:   SEQ ID NO:3
12-1759-1 DNA:   SEQ ID NO:5
```

Sequence identity at DNA level

| | 12-1758-1 | 12-1759-1 | 12-1761-1 |
|---|---|---|---|
| 12-1758-1 | | 99 | 90 |
| 12-1759-1 | | | 90 |
| 12-1761-1 | | | |

Protein sequence alignment 12-1761-1 protein: SEQ ID NO:2
12-1758-1 protein: SEQ ID NO:4
12-1759-1 protein: SEQ ID NO:6

Sequence identity at protein level

| | 12-1758-1 | 12-1759-1 | 12-1761-1 |
|---|---|---|---|
| 12-1758-1 | | 100 | 90 |
| 12-1759-1 | | | 90 |
| 12-1761-1 | | | |

Figure 9A

DNA sequence of PCV2 isolate 12-1761-1 (SEQ ID NO:1)
GGCCAGATCCTCCGCCGCCGCCCCTGGCTCGTCCACCCCCGCCACCGTTACCGCTGGGTAAGGAA
AAATGGCATCTTCAACACCCGCCTATCCCGCACCTTCGGATATACTATCAAGCGAACCACAGTCA
GAACGCCCTCCTGGGCGGTGGACATGATGAGATTCAATATTAATGACTTTCTTCCCCCAGGAGGG
GGCTCAAACCCCCGCTCTGTGCCCTTTGAATACTACAGAATAAGAAAGGTTAAGGTTGAATTCTG
GCCCTGCTCCCCGATCACCCAGGGTGACAGGGGAGTGGGCTCCAGTGCTGTTATTCTAGATGATA
ACTTTGTAACAAAGGCCACAGCCCTCACCTATGACCCCTATGTAAACTACTCCTCCCGCCATACC
ATAACCCAGCCCTTCTCCTACCACTCCCGCTACTTCACCCCCAAACCTATCCTAGATTCCACTAT
TGATTACTTCCAACCAAACAACAAAAGAAACCAGCTGTGGCTAAGACTACAAACTGCTGGAAATG
TAGACCACGTAGGCCTCGGCACTGCATTCGAAAACAGTATATACGACCAGGAATACAATATCCGT
GTAACCATGTATGTACAATTCAGAGAATTTAATCTTAAAGACCCCCCACTTAACCCTTAA Protein sequence of PCV2 isolate 12-1761-1 (SEQ ID NO:2)
GQILRRRPWLVHPRHRYRWVRKNGIFNTRLSRTFGYTIKRTTVRTPSWAVDMMRFNIND
FLPPGGGSNPRSVPFEYYRIRKVKVEFWPCSPITQGDRGVGSSAVILDDNFVTKATALT
YDPYVNYSSRHTITQPFSYHSRYFTPKPILDSTIDYFQPNNKRNQLWLRLQTAGNVDHV
GLGTAFENSIYDQEYNIRVTMYVQFREFNLKDPPLNP DNA sequence of PCV2 isolate 12-1758-1 (SEQ ID NO:3)
GGCCAAATCCTCCGCCGCCGCCCCTGGCTCGTCCACCCCCGCCACCGCTACCGATGGAGAAGGAA
AAATGGCATCTTCAACACCCGCCTCTCCCGCACCTTCGGATATACTGTCAAGGCTACCACAGTCA
GAACGCCCTCCTGGGCGGTGGACATGATGAGATTTAATCTTGACGACTTTGTTCCCCCGGGAGGG
GGGACCAACAAAATCTCTATACCCTTTGAATACTACAGAATAAGAAAAGTTAAGGTTGAATTCTG
GCCCTGCTCCCCCATCACCCAGGGTGATAGGGGAGTGGGCTCCACTGCTGTTATTCTAGATGATA
ACTTTGTACCAAAGGTCAATGCCCAAACCTATGACCCATATGTAAACTACTCCTCCCGCCATACA
ATCCCCCAACCCTTCTCGTACCACTCCCGTTACTTCACACCCAAACCTGTTCTTGACTCCACTAT
TGATTACTTCCAACCAAATAACAAAAGGAATCAGCTTTGGCTGAGGCTACAAACCTCTAGAAATG
TGGACCACGTAGGCCTCGGCACTGCGTTCGAAAACAGTATATACGACCAGGACTACAATATCCGT
GTAACCATGTATGTACAATTCAGAGAATTTAATCTTAAAGACCCCCCACTTAAACCCTAA Protein sequence of PCV2 isolate 12-1758-1 (SEQ ID NO:4)
GQILRRRPWLVHPRHRYRWRRKNGIFNTRLSRTFGYTVKATTVRTPSWAVDMMRFNLDDF
VPPGGGTNKISIPFEYYRIRKVKVEFWPCSPITQGDRGVGSTAVILDDNFVPKVNAQTYD
PYVNYSSRHTIPQPFSYHSRYFTPKPVLDSTIDYFQPNNKRNQLWLRLQTSRNVDHVGLG
TAFENSIYDQDYNIRVTMYVQFREFNLKDPPLKP

Figure 9B

DNA sequence of PCV2 isolate 12-1759-1 (SEQ ID NO:5)
GGCCAGATCCTCCGCCGCCGCCCCTGGCTCGTTCACCCCCGCCACCGCTACCGTTGGAGAAGGAA
AAATGGCATCTTCAACACCCGCCTCTCCCGCACCTTCGGATATACTGTCAAGGCTACCACAGTCA
GAACGCCCTCCTGGGCGGTGGACATGATGAGATTTAATCTTGACGACTTTGTTCCCCCGGGAGGG
GGGACCAACAAAATCTCTATACCCTTTGAATACTACAGAATAAGAAAAGTTAAGGTTGAATTCTG
GCCCTGCTCCCCCATCACCCAGGGTGATAGGGGAGTGGGCTCCACTGCTGTTATTCTAGATGATA
ACTTTGTACCAAAGGTCAATGCCCAAACCTATGACCCATATGTAAACTACTCCTCCCGCCATACA
ATCCCCCAACCCTTCTCCTACCACTCCCGTTACTTCACACCCAAACCTGTTCTTGACTCCACTAT
TGATTACTTCCAACCAAATAACAAAAGGAATCAGCTTTGGCTGAGGCTACAAACCTCTAGAAATG
TGGACCACGTAGGCCTCGGCACTGCGTTCGAAAACAGTATATACGACCAGGACTACAATATCCGT
GTAACCATGTATGTACAATTCAGAGAATTTAATCTTAAAGACCCCCCACTTAAACCCTAA Protein sequence of PCV2 isolate 12-1759-1 (SEQ ID NO:6)
GQILRRRPWLVHPRHRYRWRRKNGIFNTRLSRTFGYTVKATTVRTPSWAVDMMRFNLDDF
VPPGGGTNKISIPFEYYRIRKVKVEFWPCSPITQGDRGVGSTAVILDDNFVPKVNAQTYD
PYVNYSSRHTIPQPFSYHSRYFTPKPVLDSTIDYFQPNNKRNQLWLRLQTSRNVDHVGLG
TAFENSIYDQDYNIRVTMYVQFREFNLKDPPLKP

METHOD FOR PORCINE CIRCOVIRUS PRODUCTION AND PCV2 VACCINES

CROSS-REFERENCE TO RELATED APPLICATIONS

This application is a continuation of U.S. application Ser. No. 15/154,028 filed on May 13, 2016, which claims priority to U.S. provisional application 62/161,457 filed on May 14, 2015.

FIELD OF THE INVENTION

This invention relates to a method for rapid production of PCV2 such that an optimum yield of the virus can be obtained. This invention also relates to the vaccines useful against PCV2 which includes the PCV2 propagated using such a method.

BACKGROUND OF THE INVENTION

A family of viruses, named Circoviridae, found in a range of plant and animal species and commonly referred to as circoviruses, are characterized as round, non-enveloped virions with mean diameters from 17 to 23.5 nm containing circular, single-stranded deoxyribonucleic acid (ssDNA). The ssDNA genome of the circoviruses represents the smallest viral DNA replicons known. As disclosed in WO 99/45956, at least six viruses have been identified as members of the family according to The Sixth Report of the International Committee for the Taxonomy of Viruses (Lukert et al. 1995, The Circoviridae, pp. 166-168. In Murphy, et al. (eds.) Virus Taxonomy, Sixth Report of the International Committee on Taxonomy of Viruses, Arch. Virol. 10 Suppl.).

Animal viruses included in the family are chicken anemia virus (CAV); beak and feather disease virus (BFDV); porcine circovirus (PCV); and pigeon circovirus. PCV was originally isolated from porcine kidney cell cultures. PCV replicates in the cell nucleus and produces large intranuclear inclusion bodies (Murphy et al., 1999, Circoviridae p. 357-361, Veterinary Virology, 3rd ed. Academic Press, San Diego). There are currently two recognized types of PCV, PCV type 1 (PCV1) and PCV type 2 (PCV2). PCV1, isolated as a persistent contaminant of the continuous porcine kidney cell line PK-15 (ATCC CCL31), does not cause detectable cytopathic effects in cell culture and fails to produce clinical disease in pigs after experimental infection (Allan G., 1995, Vet. Microbiol 44: 49-64; Tischer et al., 1982, Nature 295:64-66; Tischer et al., 1986, Arch. Virol 91:271-276).

Unlike PCV1, PCV2 was initially associated with clinical diseases in the 1990s (Allan et al., 1998, J. Vet. Diagn. Invest. 10 (1), 3-10; Harding et al., 1998, J. Swine Health Prod. 6, 249-254; Le Cann et al., 1997, Piglet wasting disease, Vet. Rec. 141, 600; Segales et al., 1997, Vet. Rec. 141, 600-601) and today it remains of economic importance in the swine industry worldwide.

Clinical signs of PCV2 infection manifest in a variety of ways including postweaning multisystemic wasting syndrome (PMWS), respiratory disease (porcine respiratory diseases complex, PRDC), porcine dermatitis and nephropathy syndrome (PDNS), enteritis, sometimes a combination of these in growing pigs, and reproductive failure in breeding age animals (Opriessnig et al., 2007, J. Vet. Diagn. Invest. 19 (6), 591-615). All these syndromes are often referred to as porcine circovirus diseases (PCVD) (Kekarainen, 2014, J. General Virology, 95, 1734-1742). There is evidence that PCV2 is ubiquitous and was present many years prior to the onset of clinical PCVD (Rose et al., Virus Research, 2012, 164, 78-89). Even though PDNS was reproduced in gnotobiotic pigs in the absence of PCV2 (Krakowka et al., 2008, Am. J. Vet. Res. 69, 1615-1622), pigs with clinical PDNS possess high levels of PCV2-specific antibodies, which are implicated in disease progression (Thomson et al., 2002, J. Vet. Med. A: Physiol. Pathol. Clin. Med. 49, 430-437; Wellenberg et al., 2004, Vet. Microbiol. 99 (3-4), 203-214). A more subtle manifestation of PCV2 infection is poor growth performance in apparently healthy herds (Horlen et al., 2008, J. Am. Vet. Med. Assoc. 232 (6), 906-912). More recently, a novel peracute syndrome has been described, termed acute pulmonary edema (APE), which appeared in vaccinated herds (Cino-Ozuna et al., 2011, J. Clin. Microbiol. 49 (5), 2012-2016). Unlike previously described syndromes, which are slow and progressive, APE is characterized by acute respiratory distress in apparently healthy animals followed by almost immediate death.

As many as thirteen open reading frames (ORFs) have been identified in the PCV2 genome. ORF1 (Meehan et al., 1998, Journal of General Virology 79(9):2171-2719; Meehan et al., 1997, J Gen Vir. vol. 78, pp. 221-227) comprises the nucleotides 398-1342 (GenBank Accession No. AF055392) and has the potential to encode a protein with a predicted molecular weight of 37.7 kD. ORF2 (Meehan et al., 1998; Meehan et al., 1997) comprises the nucleotides 1381-1768 joined to 1-314 (GenBank Accession No. AF055392) and may encode a protein with a predicted molecular weight of 27.8 kD. Further description of the PCV2 ORFs 1-13 may be found in U.S. Pat. Nos. 7,144,698, 7,192,594, 7,504,206, and 7,741,039. ORF1 gene encodes Rep and Rep' proteins, which are related to virus replication. It is known that ORF2 gene encodes immunogenic structure capsid protein of PCV2, which is used to induce immune response in organisms.

Based on sequence analyses of PCV2 isolates, they can be further divided into three main genotypes (PCV2a-c). PCV2a and PCV2b have been documented worldwide (Segalés et al., 2008, Vet. Rec. 162 (26), 867-868), PCV2c has been documented in archived samples from Denmark (Dupont et al., 2008, Vet. Microbiol. 128 (1-2), 56-64).

Inactivated PCV2 vaccine is the most common commercially available PCV2 vaccine, such as CIRCOVAC (Merial), INGELVAC CircoFLEX (Boehringer Ingelheim Vetmedica), SUVAXYN PCV2 (Fort Dodge), which are based on inactivated PCV2. Published studies to date on PCV2 used either tissue homogenate or cultured virus derived from field isolates. Tischer et al. (1987, Arch Virol. 96:39-57) report that porcine kidney cells are stimulated to entry to the S phase in the cell cycle by D-glucosamine treatment. However, the treatment must be performed with caution because D-glucosamine is toxic for cell culture (see, Allan et al., 2000, J. Vet. Diagn. Investigation 12:3-14).

There is a remaining need for methods for culturing circovirus including, for example, PCV1, PCV2 and other circoviruses, such that circovirus in high yield is possible. Such methods would be advantageous, in particular for preparation of PCV2 antigens as vaccines directed against PMWS. The present invention addresses that need.

Citation or identification of any document in this application is not an admission that such document is available as prior art to the present invention.

SUMMARY OF THE INVENTION

This invention provides an improved and simplified method for rapid production of PCV2 such that an optimum yield of the virus can be obtained. The method encompasses infecting host cells with a circovirus, culturing and expanding the infected cells through passages, and isolating, collecting or harvesting the circovirus.

In the various embodiments of this method of the invention, the circovirus can be PCV2 and the host cell strain can be PK15 (Porcine Kidney), although the method should not be construed as to be applicable solely to this strain of circovirus/host cell combination.

One embodiment of the invention is a method of producing circovirus in yields that may be useful, for example, in the preparation of a vaccine, encompassing the steps of preparing PK15 cells for infection, infecting the PK15 cells with PCV2, culturing and expanding the PK15 cells through passages, and isolating, collecting or harvesting PCV2.

In one embodiment of the invention, the infection of PCV2 may be carried out in the presence or absence of glucosamine.

In another embodiment of the invention, the PK15 cells may be trypsinized at the end of each passage. The PCV2 may be harvested for vaccine preparation at any passage, or between passage 2 to passage 10. The PCV2 may be collected or harvested by sonication and subsequent removal of the cell debris.

In another embodiment of the invention, the PCV2 infected PK15 cells may be incubated at 36±2° C. The incubation period for viral growth may range from 2-8 days.

In yet another embodiment of the invention, the virus split ratio (VSR) utilized may range from 4-9 for optimum yield of the virus.

Although porcine circovirus can be detected as a contaminating agent in pig tissue cultures, successful large-scale batch cultures of the virus require streamlined process to obtain optimal and high yields. The object of the present invention, therefore, was to develop a method for speeding up the cultivation of a circovirus such as a porcine circovirus in vitro. It was intended to increase virus yield of a cell culture for the production of a vaccine that may require inactivated PCV or an avirulent PCV strain (e.g. through selection of an avirulent PCV strain after adaptation to various cell cultures and/or after treatment of infected cell cultures with mutagens or after genetic modification of the PCV) as live vaccine. There is a need for methods that can give rapid results, rather than the labor-intensive and time-consuming methods currently employed for that purpose.

These and other embodiments are disclosed or are obvious from and encompassed by, the following Detailed Description.

BRIEF DESCRIPTION OF DRAWINGS

The following detailed description, given by way of examples, but not intended to limit the invention solely to the specific embodiments described, may best be understood in conjunction with the accompanying drawings, incorporated herein by reference, in which:

FIG. 7 is a table showing the SEQ ID NO assigned to each DNA and protein sequence.

FIGS. 8A-C show the DNA and protein sequence alignments of PCV2A and PCV2B.

FIGS. 9A-B list the DNA and protein sequences.

DETAILED DESCRIPTION

Figure 1:
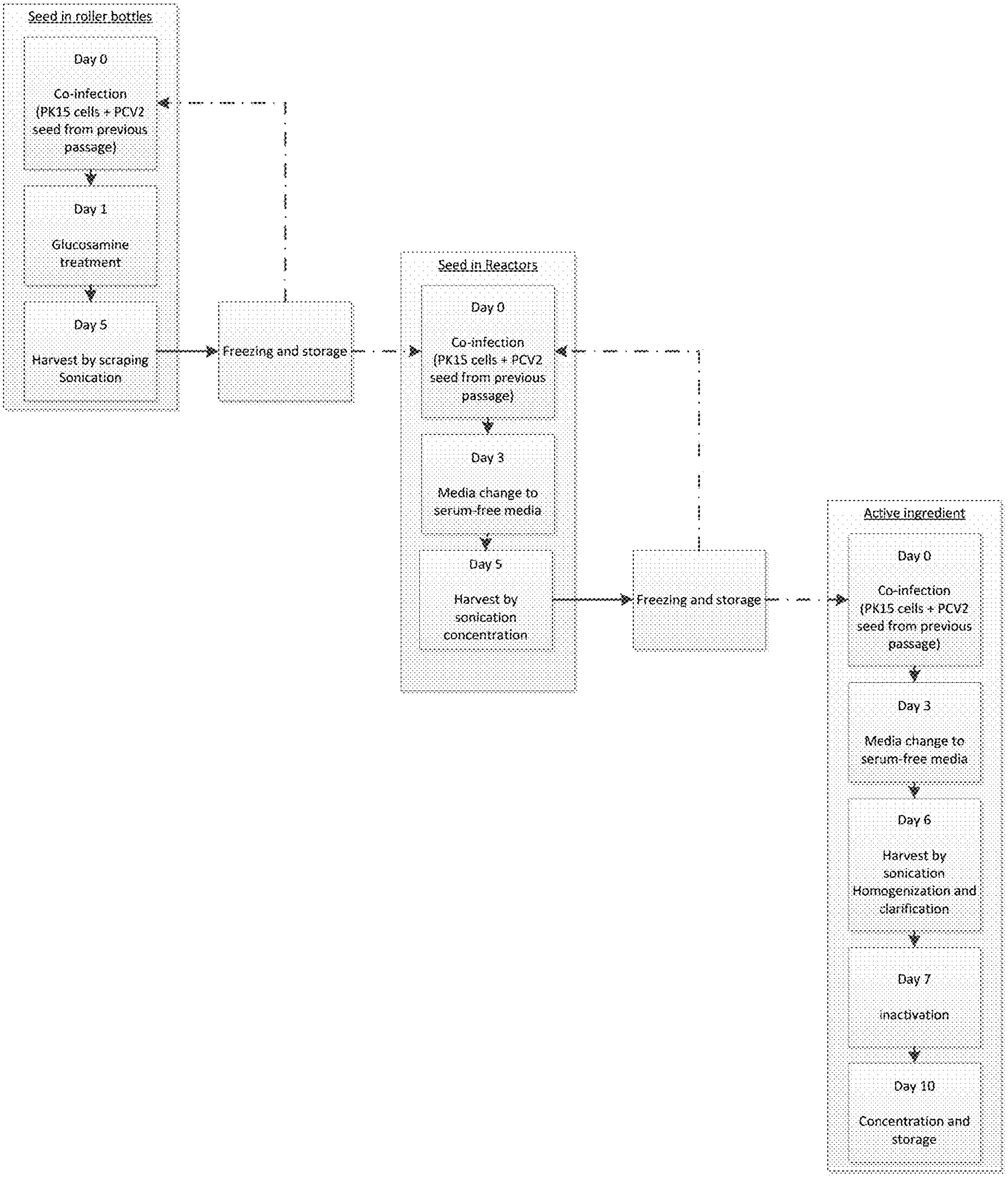
FIG. 1 illustrates the current PCV2 production process.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "flow cytometer" as used herein refers to any device that will irradiate a particle suspended in a fluid medium with light at a first wavelength, and is capable of detecting a light at the same or a different wavelength, wherein the detected light indicates the presence of a cell or an indicator thereon. The "flow cytometer" may be coupled to a cell sorter that is capable of isolating the particle or cell from other particles or cells not emitting the second light. The indicator on the cell surface may be an antibody coupled to a fluorophore such as, but not limited to, FITC.

The term "host cell" as used herein refers to an isolated cell that is a host for the infection and replication of a virus, preferably a circovirus. A "host cell" denotes a prokaryotic or eukaryotic cell. The "host cell" may be genetically altered, or is capable of being genetically altered by administration of an exogenous polynucleotide, such as a recombinant plasmid or vector. The "host cell" may be a cell established in stable lineage without any genetic modifications, only by repeated culture passages. The "host cell" may be primary cells that are neither modified nor stable. When referring to genetically altered cells, the term refers both to the originally altered cell and to the progeny thereof.

The term "PK15 cells" as used herein refers to any porcine kidney cell line. The term "PK15 cells" include any PK15 cells established in stable lineage without any genetic modifications, only by repeated culture passages, including for example, PK15 parent cells, PK15-C1 cells and PK15-A2 cells. The "PK15 cells" may be genetically altered, or are capable of being genetically altered by administration of an exogenous polynucleotide, such as a recombinant plasmid or vector.

The term "PCV2" as used herein refers to any subtype PCV2, including for example PCV2a, PCV2b and PCV2c.

The term "PCV2 vaccine" as used herein includes an agent which may be used to stimulate the immune system of pigs against PCV2 virus.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle, buffalos), swine (e.g., pig), ovine (e.g., sheep), caprine (e.g., goats), camelids (e.g., lamas), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages. The term "pig" or "piglet" means an animal of porcine origin, while "sow" refers to a female of reproductive age and capability.

The term "seed culture" or "seed" as used herein refers to a culture of host cells infected with a selected virus such as a circovirus and which is then incubated for a period to allow the titer of virus to increase. Typically, but not necessarily, the volume of a seed culture is less than the volume of the subsequent main culture or fermentation medium that receives the seed culture.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

Abbreviations

PK, porcine kidney; PCV, Porcine CircoVirus; PK15, porcine kidney cells; ELISA, enzyme-linked immunosorbant assay; Mab, monoclonal antibody; FITC, Fluoresceine isothiocyanate; IgG, immunoglobulin G; PBS, phosphate buffered saline; MEDM, dulbecco minimum essential medium; FBS, fetal bovine serum; BS, bovine serum.

The present invention provides improved and simplified method for rapid production of porcine circovirus such that an optimum yield of the virus can be obtained. The methods of the invention, however, are generally applicable to any other strain or type of circovirus growing on cell culture, especially in batch culture procedures. The methods of the invention are particularly useful for the production of the porcine circovirus PCV2.

The methods of the invention offer a viral yield useful, for example, for the production of a vaccine, while minimizing the incubation period of the cells with attendant cost reductions.

One embodiment of the invention is a method of producing circovirus in yields that may be useful, for example, the preparation of a vaccine, encompassing the steps of preparing PK15 cells for co-infection, infecting the PK15 cells with PCV2, culturing and expanding the PK15 cells through passages, and isolating, collecting or harvesting PCV2.

Traditional methods of virus production or amplification utilize the strategy in which a non-infected cell is infected with the virus and then killed so was to release its viral content. The methods work but are plagued by a decrease in infectious titer over the different passages. This decrease in infectious titer is then compounded by the amount of seed that needs to be used so as to improve the MOI. This impacts both AI (active ingredient) and seeds yields. As seed becomes less and less potent, more lab capacity would have to be dedicated to the production of seeds which affects the throughput of the virus product.

The method of the invention uses a persistently infected cell to amplify the virus. The method does not require subsequent infection of PK15 cells after the initial cell passage and infection. The method offers streamlined process in which a persistently infected cell line is maintained throughout the entire amplification.

In one embodiment of the invention, the infection of PCV2 may be carried out in the presence or absence of glucosamine. PCV2 infection rate may be at a level from about 0.005 MOI (multiplicity of infection) to about 1.0 MOI.

PCV2 can be cultured in the PK15 culture to a titer of at least $1\times10^2$ $TCID_{50}$ (tissue culture infective doses—fifty percent), $1\times10^3$ $TCID_{50}$, $1\times10^4$ $TCID_{50}$, $1\times10^5$ $TCID_{50}$, at least $1\times10^6$ $TCID_{50}$, at least $1\times10^7$ $TCID_{50}$, at least $1\times10^9$ $TCID_{50}$, at least $1\times10^{10}$ $TCID_{50}$, or at least $1\times10^{15}$ $TCID_{50}$. The titer may be calculated by any titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose).

In another embodiment of the invention, the PK15 cells may be trypsinized at the end of each passage. The trypsinization of the infected PK15 cells may be carried out for about 10 min, about 15 min, about 20 min, about 30 min, about 45 min, or about 60 min.

The PCV2 may be collected or harvested for seed culture preparation or vaccine preparation at any passage after the initial cell passage and infection, for example, at the end of the second passage (X+2), the third passage (X+3), the fourth passage (X+4), the fifth passage (X+5), the sixth passage (X+6), the seventh passage (X+7), the eighth passage (X+8), the ninth passage (X+9), the tenth passage (X+10), and passage beyond (X+n, wherein n is greater than 10).

The PCV2 may be isolated, collected or harvested from the PK15 infected cells of the culture using methods known to those of ordinary skill in the art. In particular, virus can be isolated from extracts of infected cells obtained by any of the typical methods for virus extraction, such as sonication, centrifugation, and freeze-thaw. The virus-containing fluid batches collected from the cell culture are pooled, freed from cell debris by any known method, e.g. by settling followed by decantation, or using a separator or filter, or else by centrifugal action.

In another embodiment of the invention, PCV2 infected PK15 cells are incubated and maintained at 36±2° C. The incubation period for viral growth may range from 2-8 days, for example, for 2 days, 3 days, 4 days, 5 days, 6 days, 7 days, or 8 days.

In yet another embodiment of the invention, the virus split ratio (VSR) may range from 4-9 for optimum yield of the virus. The VSR value of 4, 5, 6, 7, 8, or 9 may be used to calculate the optimum volume of seed culture used to start the next passage in either a roller bottle or a bioreactor.

The preparation and maintenance of cultures of the PK15 cell line may be effected by techniques which are well known in the art. For example, cultures may be seeded at $200\times10^3$ cells ml in a plastic flask or bioreactor, or 50 million cells in a roller bottle in an appropriate medium, such as DMEM (Dulbecco's minimum essential medium), and then incubated, e.g., at approximately 37° C. The D-MEM medium may be supplemented with 5% BS (bovine serum).

In the method of the present invention, the expansion of the persistently infected PK15 cells for the production of a PCV2 vaccine results in improved yields of virus providing a competitive advantage to any traditional method of continuous cell infection for vaccine production or other purposes. In particular, the method of expanding the persistently infected PK15 cells allows production of high yields of virus and virus antigen to be used in vaccine production, PCV2 seed culture preparation or diagnostic assays.

The present invention also relates to a method of isolating PCV2 from a sample. This method involves providing a biological sample infected with PCV2, providing a PK15 cell culture, incubating the culture with the biological sample under conditions effective to allow the virus to infect the culture, and isolating the virus from the culture.

Suitable biological samples include blood, mucosal scrapings, semen, tissue biopsy, embryonal tissues, secretions and excretions, and swabs of bodily fluids.

Another aspect of the present invention is a method for identifying PCV2 in a sample. This method involves providing a biological sample potentially containing PCV2, providing a PK15 cell culture, incubating the culture with the biological sample under conditions effective to allow any of the virus present in the biological sample to infect the culture, and identifying the presence of any of the virus in the culture.

Suitable methods for identifying the presence of the virus in the culture, i.e., demonstrating the presence of viral proteins in the culture, include immunofluorescence tests, which may use a monoclonal antibody against one of the viral proteins or polyclonal antibodies (von Bulow et al., in Diseases of Poultry, 10th edition, Iowa State University Press, pp. 739-756, 1997), polymerase chain reaction (PCR) or nested PCR (Soine et al., Avian Diseases 37:467-476, 1993), ELISA (von Bulow et al., in Diseases of Poultry, 10th edition, Iowa State University Press, pp. 739-756, 1997), virus neutralization, or any of the common histochemical methods of identifying specific viral proteins.

Yet another aspect of the present invention is a method for quantifying PCV2 in a sample. This method involves providing a biological sample containing a quantity of PCV2, providing a PK15 cell culture, incubating the culture with the biological sample under conditions effective to replicate the virus in the culture, and titrating the quantity of the virus in the culture.

Titrating the quantity of the virus in the culture may be effected by techniques known in the art, as described in Villegas et al., "Titration of Biological Suspensions," In: A Laboratory Manual for the Isolation and Identification of Avian Pathogens, 3.sup.rd Ed., Purchase et al., Eds., Kendall/Hunt Publishing Co., Dubuque, Iowa, pp. 186-190 (1989).

The present invention relates to a high titer vaccine formulation for PCV2 which includes an immunologically effective amount of PCV2 propagated in PK15 cell culture.

One embodiment of the present invention is a live vaccine. Live attenuated vaccines may be produced by passaging and propagating PCV2 in an appropriate cell culture, e.g., the PK15 culture. The vaccines of the present invention containing a live attenuated PCV2 strain can be prepared and marketed in the form of a suspension or as a lyophilized product in a manner known per se.

Another embodiment of the present invention is an inactivated vaccine which includes one or more isolates of inactivated PCV2 propagated in PK15 culture.

In one aspect of the embodiment, the PCV2 may be any PCV2 strains disclosed in U.S. Pat. Nos. 6,368,601, 6,391,314, 6,660,272, 7,122,192, 7,144,698, 7,192,594, 7,504,206, 7,741,039, 7,833,783, 7,803,613, 7,803,926, 7,211,379, 6,517,843. The PCV2 may be the strains Imp. 1008, Imp. 1010, Imp999, Imp. 1011-48285, Imp. 1011-48121, Imp. 1103, Imp. 1121 as disclosed in U.S. Pat. Nos. 7,211,379 and 7,122,192. The PCV2 strain may be the strain Imp. 1010) (CIRCOVAC®).

In another aspect of the embodiment, the PCV2 may contain a polynucleotide encoding an ORF2 protein that is found in U.S. Pat. Nos. 6,368,601, 6,391,314, 6,660,272, 7,122,192, 7,144,698, 7,192,594, 7,504,206, 7,741,039, 7,833,783, 7,803,613, 7,803,926, 7,211,379, 6,517,843, 6,943,152, 6,217,883, 6,953,581, 6,497,883, 7,109,025.

In yet another aspect of the embodiment, the ORF2 protein has at least 70%, 75%, 80%, 85%, 90%, 95%, 96%, 97%, 98%, 99% or 100% sequence identity to a polypeptide having the sequence as set forth in SEQ ID NO:2, 4, or 6. In another aspect of the embodiment, the ORF2 is encoded by a polynucleotide having at least 70%, 75%, 80%, 85%, 90%, 95%, 96%, 97%, 98%, 99% or 100% sequence identity to a polynucleotide having the sequence as set forth in SEQ ID NO:1, 3, or 5.

Inactivation of PCV2 (to eliminate reproduction of the virus) for use in the vaccine of the present invention can be achieved, in general, by chemical or physical means (see U.S. Pat. No. 5,728,569). Chemical inactivation can be effected by treating the virus with, for example, enzymes, formaldehyde, beta-propiolactone (BPL), ethylene-imine, binary ethylenimine (BEI), or a derivative thereof. If necessary, the inactivating compound can be neutralized after inactivation is complete. For example, material inactivated with formaldehyde can be neutralized with thiosulfate. Physical inactivation can be effected by subjecting the virus to energy-rich radiation, e.g., UV light, X-radiation, or gamma-radiation. If desired, the pH can be brought back to a value of about 7 after treatment.

The vaccine may be produced both from freshly trypsinized cell culture of PK15 cells and from one withdrawn from storage in liquid nitrogen.

The vaccines of the present invention are administered in a dose sufficient or effective to induce an immune response to PCV2. Determination of the therapeutically effective amount is routine experimentation for one of ordinary skill in the art.

The vaccines of the present invention can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They can be administered alone or with pharmaceutically or veterinarily acceptable carriers, excipients, adjuvants, or stabilizers, and can be in solid or liquid form such as, powders, solutions, suspensions, or emulsions.

The pharmaceutically or veterinarily acceptable carriers, adjuvants, stabilizers, or excipients are well known to the one skilled in the art. For example, a pharmaceutically or veterinarily acceptable carrier or stabilizers or excipient can be a 0.9% NaCl (e.g., saline) solution or a phosphate buffer. Other pharmaceutically or veterinarily acceptable carrier, adjuvant, vehicle, or excipients that can be used for methods of this invention include, but are not limited to, poly-(L- glutamate) or polyvinylpyrrolidone. The pharmaceutically or veterinarily acceptable carrier, adjuvant, stabilizers, or excipients may be any compound or combination of compounds facilitating the administration of the vaccine; the carrier, stabilizers, adjuvant, or excipient may facilitate transfection and/or improve preservation of the vaccine. Doses and dose volumes are herein discussed in the general description and can also be determined by the skilled artisan from this disclosure read in conjunction with the knowledge in the art, without any undue experimentation.

The immunogenic compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) saponin, (8) Dimethyldioctadecyl ammonium bromide (Vaccine Design p. 157), (9) Aridine (Vaccine Design p. 148) other adjuvants discussed in any document cited and incorporated by reference into the instant application, or (8) any combinations or mixtures thereof.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Some of the emulsions, such as TS6, TS7, TS8 and TS9 emulsions, are described in U.S. Pat. Nos. 7,608,279 and 7,371,395.

To stabilize the virus, a suitable stabilizer is added to the product virus-containing fluid, e.g. 4.5 to 5.5 percent sorbite by weight and 1.4 to 1.6 percent gelatose by weight, after which the liquid is lyophilized.

The PCV2 propagated in PK15 culture of the present invention may be administered in injectable dosages by solution or suspension of these materials in a physiologically acceptable diluent with a pharmaceutical or veterinarily carrier. Such carriers include sterile liquids, such as water and oils, with or without the addition of a surfactant and other pharmaceutically and veterinarily acceptable carriers, including adjuvants, excipients, or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Vaccines according to the present invention may contain combinations of the PCV2 propagated in PK15 culture and one or more unrelated swine pathogens or viruses. Suitable unrelated swine viruses include, for example, Adenovirus; Classical swine fever virus, African swine fever virus; Digestive and respiratory Coronavirus; *Cryptosporidium parvum; Eimeria* spp; *Mycoplasma haemosuis; Mycoplasma hyopneumoniae; Escherichia coli; Lawsonia intracellularis; Leptospira* spp.; *Mannheimia haemolytica; Mycobacterium* spp.; Parvovirus; *Pasteurella multocida*; Porcine cytomegolovirus; Porcine parovirus, Porcine reproductive and respiratory syndrome virus: Pseudorabies virus; Rotavirus; Sagiyama virus; *Salmonella* spp.; *Staphylococcus* spp.; Swine cytomegalovirus; Swine herpes virus; Swine influenza virus; Swine pox virus; *Toxoplasma gondii*; Vesicular stomatitis virus and virus of exanthema of swine; porcine epidemic diarrhea virus; and other isolates and subtypes of porcine circovirus.

Another aspect of the present invention is a method of immunizing swine against PCV2 which includes administering a vaccine prepared from PCV2 propagated in a PK15 cell culture in an amount effective to induce an immune response to the virus.

The seed cultures developed as a result of the use of the methods of the invention can be used to seed large volume fresh cell culture medium, in the order of 5-1000 liter volumes. In this procedure, the seed culture harvested is inoculated into a large-scale culture comprising cell culture medium.

It should be understood that the present invention is not limited to the specific compositions, equipment or methods described herein and that any composition having a formula or method steps equivalent to those described falls within the scope of the present invention. The method steps for determining the percentage of infected cells in a cell culture are merely exemplary so as to enable one of ordinary skill in the art to make the composition and use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the invention.

The invention is further described by the following non-limiting examples:

EXAMPLES

Example 1 Summary of the Current PCV2 Production

To produce PCV2 active ingredient (AI) for the preparation of inactivated PCV2 vaccine, PK15 seed culture (X passage) was used to amplify the PCV2 virus according to the procedure described below.

X+1 to X+3 Passages in Roller Bottles

On day 0, PK15 cells (Porcine Kidney) were thawed and suspended in 5% FBS (fetal bovine serum) and 300 ml DMEM (Dulbecco's minimum essential medium). The PK15 cells and the media were dispensed in roller bottles (RBs) at a density of 50 million cells/RB. PCV2 virus (the active ingredient of the licensed CIRCOVAC® vaccine, see U.S. Pat. No. 6,660,27 and U.S. Pat. No. 7,122,192) was thawed and used to infect the PK15 cells (estimated MOI=0.1). The RBs were placed at 37° C. and 0.4 rpm.

On day 1, the media was removed from the rollers. Enough 20 mM Glucosamine solution was added to each RB to cover the cell layer and then incubated for 30 min at 25° C. The glucosamine treatment is used to allow the penetration of the virus DNA into the cell's nucleus (Tischer, 1987, Archives of Virology, 96:39-57; Stevenson, 1999, Veterinary Pathology, 36:368-378). After 25 min, the glucosamine was removed and 300 ml of DMEM with 5% FBS was added to the rollers. The rollers were placed at 37° C. and 0.4 rpm.

On day 5, the rollers were harvested. Using cell scrapers, the infected monolayer was removed and the viral pool was sonicated between 5 and 25 $W \cdot s \cdot ml^{-1}$. The harvest material was frozen at −70° C. Samples were thawed and used for live titer (the procedure described in Example 3) determination before beginning the next passage.

X+4 to X+7 Passages in Reactors

To scale up the production of PCV2 viruses, the passages after X+3 were carried out in bioreactors. The bioreactors were 7 L mini-bioreactor each with 5 L media and 1.5 g/L of Cytodex1 microcarriers. The reactors contained PK15 cells at a concentration of $200\times10^3$ cells/ml.

On day 0, PK15 cells were co-infected with the PCV2 harvested from the previous passage as described above.

On day 3, the media containing DMEM and 5% FBS was removed and the serum free media (DMEM/VP-SFM) was added to the reactors.

On day 5, the cells were harvested by sonication to remove the cells from the microcarriers and the PCV2 viruses were released. The harvested material was then concentrated. Serum was added as a cryoconservator (5%) and the concentrate was frozen for storage for the next passage.

X+8 AI Process

For the AI, the process was the same up to the sonication. After sonication, the product was passed through a high pressure homogenizer to insure maximal virus release and centrifuged to remove the cell debris. The resulting product (harvest) was then inactivated using BPL (betapropiolactone) before it was concentrated. An ELISA titer determination (the procedure described in Example 3) was performed to quantify the PCV2 virus produced. The concentrate was stored at +7° C.

Discussion

The current PCV2 production process is illustrated in FIG. 1.

The PCV2 AI yield has been decreasing over time using the current protocol. It is clear that the current amplification process in which the virus was grown on PK15 cells and then harvested by disrupting the cells resulted in lower and lower live titers as the amplification progresses. An effect which is amplified by the number of passages needed.

Figure 2:
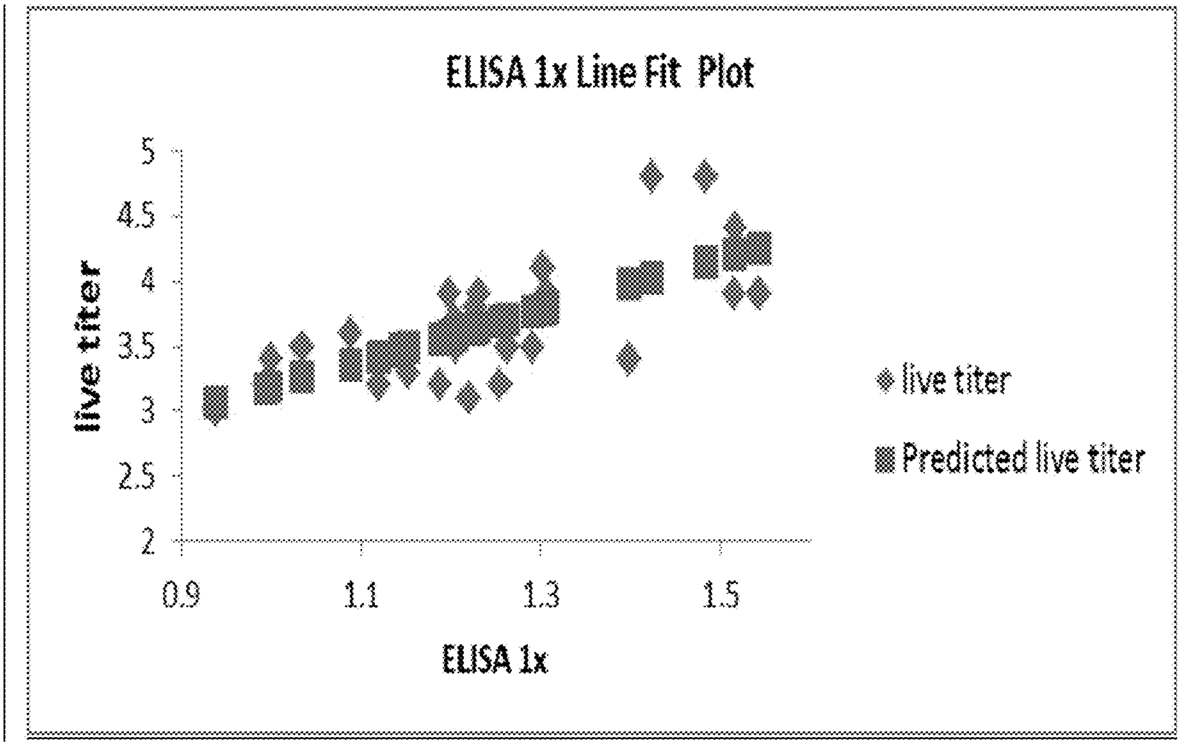
FIG. 2 illustrates the relationship between live titer before inactivation and the resulting ELISA titer after inactivation for the AI produced.

There is a relationship between live titer and ELISA titer which is shown in FIG. 2. The inability to maintain live titers impacts both AI and seeds.

Two factors seem of major importance in trying to sustain live titers: the MOI (multiplicity of infection) and the volume of seed used to inoculate the culture. Both are influencing the outcome of the culture in different ways. The quality of the culture, as defined by its final live titer, benefits from higher MOI while too much seed is going to be toxic, resulting in poor yield.

Figure 3:
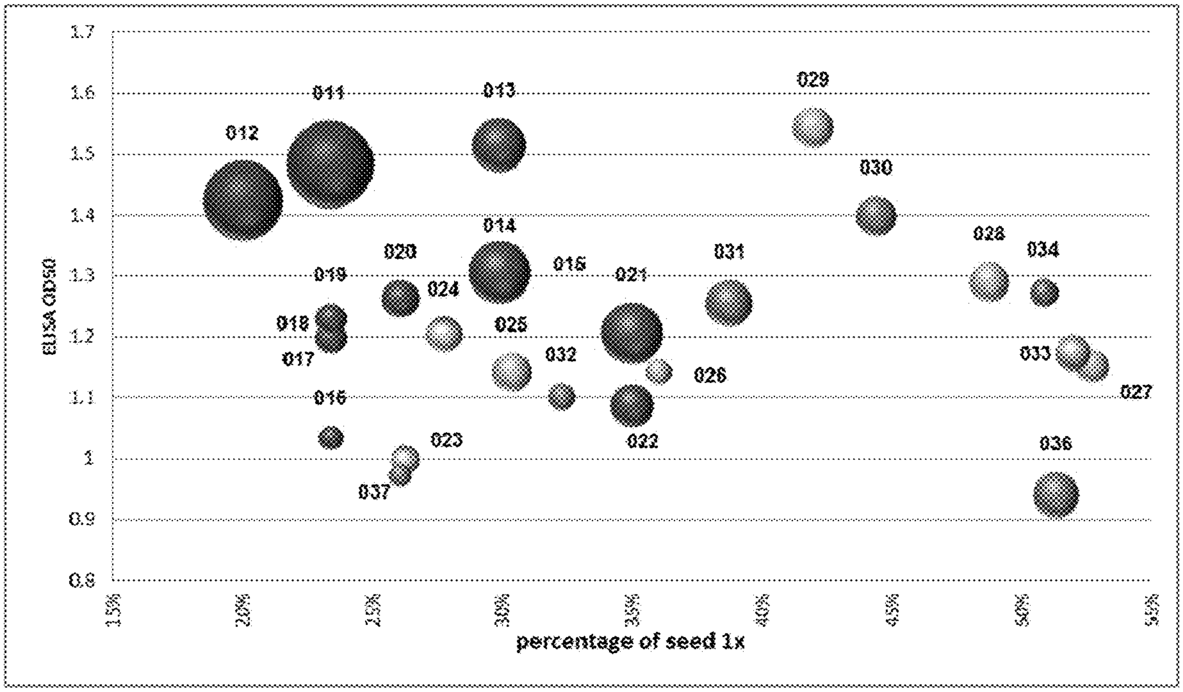
FIG. 3 illustrates the ELISA titer function of the percentage of seed used for inoculation.

As shown in FIG. 3, the ELISA titer depends on having good quality seed which results in both a greater MOI while maintaining the percentage of seed used for inoculation to a level which does not prevent virus production due to toxicity. Further analysis indicates that the percentage of seed used to inoculate the culture negatively impacts the output titers at a greater rate than the added MOI is benefiting it.

Figure 4:
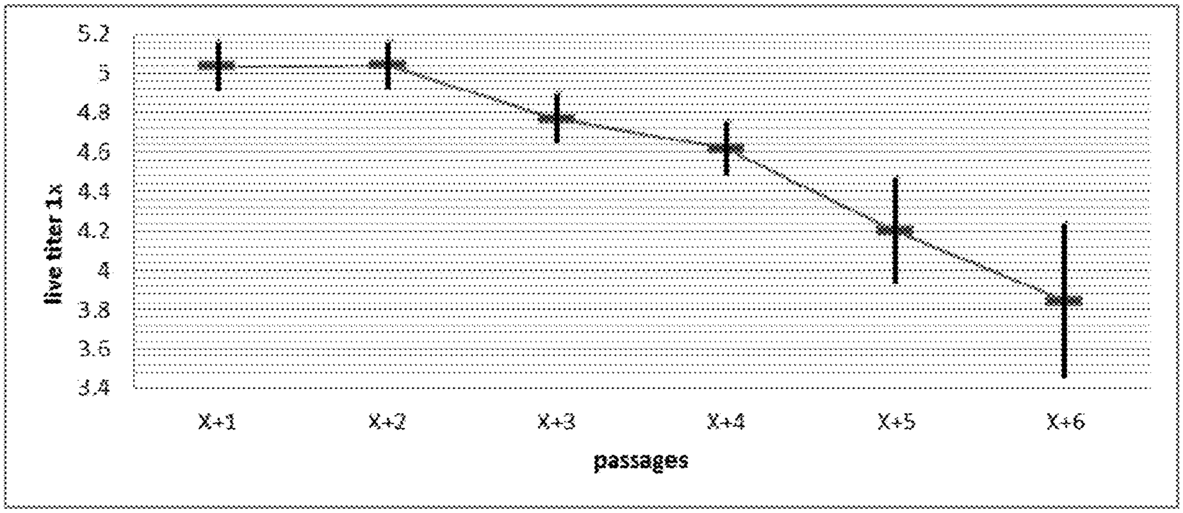
FIG. 4 illustrates the live titer evolution over seed amplification in the current protocol.

FIG. 4 shows the average titer of the seeds produced using the current method. This chart shows the inevitability of titer decline during seed amplification, an effect which is compounded by the lineage effect as shown by the increase in standard deviation when reaching the X+5 and X+6 passages. As shown, the X+6 seed average titer is about 3.8 ($1\times10^{3.8}$ $TCID_{50}$).

Example 2 Improved Method of PCV2 Production

Figure 5:
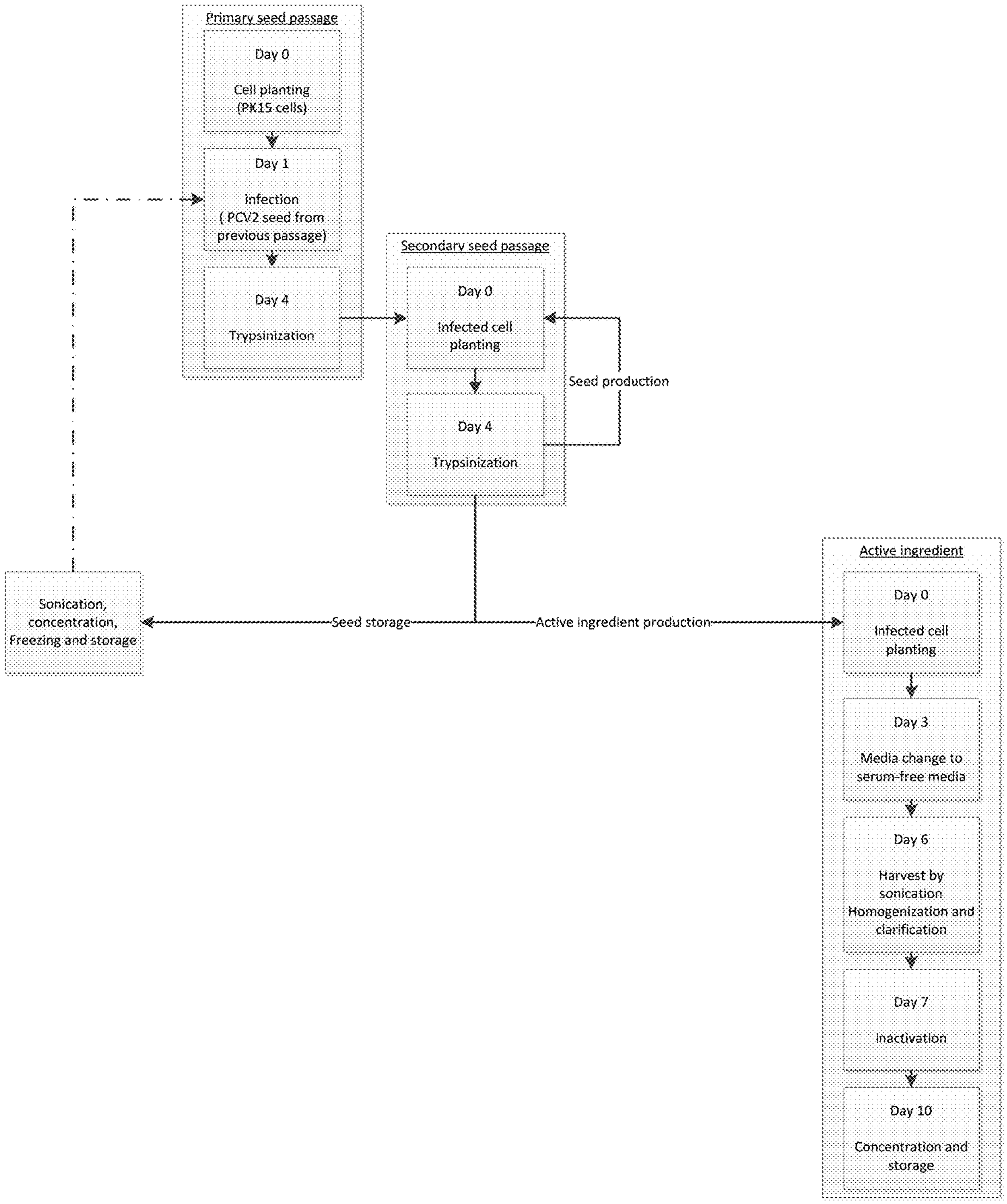
FIG. 5 illustrates the persistently infected cell line process.

To produce PCV2 active ingredient (AI) for the preparation of inactivated PCV2 vaccine or the production of PCV2 seed culture, the PK15 cells infected with PCV2 virus (X passage) were expanded to amplify the PCV2 virus (persistently infected cell line) according to the procedure described below. The persistently infected cell line process is illustrated in FIG. 5.

Initial Cell Passage and Infection

The PK15 cells from the frozen bag were thawed into a 37° C. water bath, re-suspended into growth media (DMEM with 5% FCS) and planted into RB at a density of 50 million cells per RB.

One day later, the cells were infected with 130 ml of PCV2 seed (the active ingredient of the licensed CIRCOVAC® vaccine, see U.S. Pat. No. 6,660,27 and U.S. Pat. No. 7,122,192) per RB (estimated MOI=0.1). The seed was left in contact with the treated cell layer for 30 minutes at 37° C. on a roller rack. Once the absorption finished, 170 ml of growth media was added to each RB before the roller rack was pushed back into the walk-in incubator.

Trypsinization

After 3 days of culture, the RB were observed and found to have a large amount of cell debris in suspension. Cell count showed 260 million cells per RB which is quite standard for PK15 cells. After observation, the media was removed and trypsin was used to remove the cells from the roller wall. Trypsinization of the cells was performed according to the procedure as described below.

The cell layer was rinsed with 50 ml PBS for 5-10 min. The PBS was discarded and replaced with 20 ml trypsin solution (0.1 g/l-1.0 g/l) for 20 min at 37° C. The RBs were placed at 37° C. and monitored for cloudiness of the trypsin solution as well as streaking of the cell layer. Once streaks appeared on the cell layer, the cells were shaken off the RB wall manually. The cell suspension was pipetted out of the RB and pooled into a container. 10% FCS was added to the cell suspension to neutralize the trypsin.

Post trypsinization, the cells were used to seed fresh RB at 50 million cells per RB with 300 ml fresh media and set into the incubator at 37° C.

Subsequent Passages X+2 to X+7 in Either RB or Reactor

The cells were observed daily and were trypsinized as described above once 100% confluence has been achieved (typically 2-4 days).

Post trypsinization, the cells were used to seed fresh RB at about 50 million cells per RB with 300 ml fresh media (DMEM with 5% FCS) or about $200\times10^3$ cells/ml per reactor with fresh media, and set into the incubator at 37° C.

PCV2 Virus Preparation for Seed Culture

PCV2 virus may be collected or harvested at any passage for seed (virus) storage as shown in FIG. 5. Post trypsinization, the cells were sonicated and PCV2 viruses were collected, concentrated and stored at −70° C. for storage to be used for subsequent infection of PK15 cells.

PCV2 Virus Preparation for AI Process at X+8

For the AI preparation at passage X+8, the infected cells were amplified for 3 days in DMEM with 5% serum after which the media was changed to a serum free media for three more days. Cells were removed from the microcarriers through sonication. The cell suspension was then homogenized and cell debris were removed by centrifugation. The resulting product (harvest) was then inactivated using BPL before it was concentrated. An ELISA titer determination (the procedure described in Example 3) was performed to quantify the PCV2 virus produced. The concentrate was stored at +7° C.

Results

The cell count and average titer of each passage are summarized in Table 1 below.

TABLE 1

| Sample Date | Cell passage | Virus passage | Cell count (million) | Average titer (live titer) |
|---|---|---|---|---|
| N/A | PK15 Cell + 1 | X + 2 | N/A | N/A |
| N/A | PK15 Cell + 2 | X + 3 | N/A | N/A |
| N/A | | | N/A | N/A |
| 21-April | | | 258 | 5.1 |
| 23-April | PK15 Cell + 3 | X + 4 | 42.5 | 4.3 |
| 25-April | | | 77 | 4.7 |
| 27-April | | | 186 | 4.7 |
| 29-April | PK15 Cell + 4 | X + 5 | 77 | 4.2 |
| 1-May | | | 348 | 4.6 |
| 2-May | | | 314 | 4.6 |
| 4-May | PK15 Cell + 5 | X + 6 | N/A | N/A |
| 5-May | | | 250 | 4.4 |
| 6-May | | | 291 | 4.7 |
| 8-May | PK15 Cell + 6 | X + 7 | N/A | N/A |
| 9-May | | | 311 | 4.4 |
| 10-May | | | 348 | 5 |
| 12-May | PK15 Cell + 7 | X + 8 | N/A | N/A |
| 13-May | | | 42 | N/A |
| 14-May | | | 24 | 5.1 |

The live titer results demonstrated that the new method was able to sustain live virus titer throughout the experiment to the last passage. The result of 5.1 ($1\times10^{5*1}$ $TCID_{50}$) at the last passage is more than 1 log 10 above the current live titer of the seed when the current method was used (3.8 average live titer).

Moving from the current strategy to a more streamlined process in which a persistently infected cell line is maintained throughout the entire amplification offers great advantages compared to the current process. It is simpler, faster, and involves less equipment. When producing AI, the new method removes the need for storage of large scale seed and everything coming with it (such as inventory) and dedicates the entire capacity of the lab to the production of AI.

Glucosamine Treatment

This study was designed to assess the need for the glucosamine treatment. Since the glucosamine role is to allow the transfer of the virus DNA into the cell nucleus, which is only feasible during the last stage of the cell division when glucosamine is absent, the study was designed to check if this treatment had any impact when an infected cell line was allowed to grow for 3 weeks.

A glucosamine treatment was implemented and the cell layer was treated 4 hours post-infection. In order to insure that the stream which did not have a glucosamine treatment would not benefit from more contact time with the seed, the media was replaced by fresh growth media 4 hours post infection.

After the initial cell passage and infection, half of the RB had their media harvested to be reused as part of the comparison between passing the cells with the spent media or not using the spent media (this is referred as the 2 steams).

Post trypsinization, half of the cells were re-suspended into the spent media and 60 ml of this cell suspension was used to seed new RB at 50 million cells per RB. 240 ml of fresh growth media was then added to the RB before they were put on a roller rack in the incubator (this is the R stream). The remainder of the cells were used to seed fresh RB at 50 million cells per RB with fresh media only (this is the D stream) and set into the incubator.

Other cell passages (X+2 and beyond) for the R stream: the cells were observed daily and were trypsinized once 100% confluence has been achieved. Prior to trypsinization, the spent media was aseptically collected. The trypsinized cells were re-suspended into the spent media which was supplemented with fresh media. Fresh RBs were seeded at 50 million cells per RB containing 20% spent media.

Other cell passages (X+2 and beyond) for the D stream: The cells are observed daily and are trypsinized once 100% confluence has been achieved. Prior to trypsinization the spent media is aseptically discarded. Fresh RBs are seeded at 50 million cells per RB with 300 ml of fresh media.

The cell count and average live titer of D and R streams are shown in Table 2 below.

TABLE 2

| | | | D stream | | R stream | |
|---|---|---|---|---|---|---|
| Sample Date | Cell passage | Virus passage | Cell count (million) | Average titer (live titer) | Cell count (million) | Average titer (live titer) |
| N/A | PK15 Cell + 1 | X + 2 | N/A | N/A | N/A | N/A |
| N/A | PK15 Cell + 2 | X + 3 | N/A | N/A | N/A | N/A |
| N/A | | | N/A | N/A | N/A | N/A |
| 21-April | | | 258 | 5.1 | N/A | N/A |
| 23-April | PK15 Cell + 3 | X + 4 | 42.5 | 4.3 | 34.6 | 4.2 |
| 25-April | | | 77 | 4.7 | 81.4 | 4.6 |
| 27-April | | | 186 | 4.7 | 132 | 4.6 |
| 29-April | PK15 Cell + 4 | X + 5 | 77 | 4.2 | 112 | 4.6 |
| 1-May | | | 348 | 4.6 | 279 | 4.3 |
| 2-May | | | 314 | 4.6 | 243 | 4.6 |
| 4-May | PK15 Cell + 5 | X + 6 | N/A | N/A | N/A | N/A |
| 5-May | | | 250 | 4.4 | 177 | 4.2 |
| 6-May | | | 291 | 4.7 | 230 | 4.7 |
| 8-May | PK15 Cell + 6 | X + 7 | N/A | N/A | N/A | N/A |
| 9-May | | | 311 | 4.4 | 244 | 4.5 |
| 10-May | | | 348 | 5 | 373 | 4.9 |
| 12-May | PK15 Cell + 7 | X + 8 | N/A | N/A | N/A | N/A |
| 13-May | | | 42 | N/A | 220 | N/A |
| 14-May | | | 24 | 5.1 | 228 | 5 |

Table 3 below lists the live titer pre-inactivation and the ELISA titer post inactivation for both streams.

TABLE 3

| | No glucosamine | glucosamine |
|---|---|---|
| Live titer ($log_{10}$) | 5 | 4.7 |
| ELISA | 1.8 | 1.7 |

The results showed that there is no difference between the D and R streams. There is no benefit in recycling the spent media.

Trypsin Treatment

The goal of the experiment was to investigate the effect of trypsin on the live titer of the harvested seed, particularly if longer exposure to the trypsin solution has deleterious effect.

The cells were left in contact with the trypsin solution for 15, 30, 45 and 60 minutes. The resulting cell suspension was re-suspended in the spent media and sampled for titration. The results are shown in Table 4 below.

TABLE 4

| | trypsinization study (time in minutes) | | | |
|---|---|---|---|---|
| Time (min) | 15 | 30 | 45 | 60 |
| average titer | 4.1 | 4.3 | 4.4 | 4.3 |

The results indicate that the trypsin experiments did not impact the live titer of the product in any measurable manner.

Sonication Treatment

The goal of the experiment was to investigate the effect of repeated sonication on the live titer. The assumption was that subsequent passes through the sonitube may initially result in higher release of live virus followed by a decrease of the live titer as more energy was added to the system.

The spent media was harvested and the cells trypsinized. The resulting cell suspension was then repeatedly sonicated on a 35 kHz sonitube at 100% amplitude at such a flow rate so as to maintain a difference of temperature between the inlet and outlet of the sonitube at around 2° C. The sonicated material was sampled after each pass for titration. The results are shown in Table 5 below.

TABLE 5

| sonication study (ΔT ° C./cumulative dissipated energy W · s/ml) | | | | | | | | | | |
|---|---|---|---|---|---|---|---|---|---|---|
| ΔT ° C. | 2.2 | 2.5 | 2.4 | 2.5 | 2.5 | 2.3 | 2.2 | 2.3 | 2.8 | 2.4 |
| cumulative dissipated energy W · s/ml | 9.2 | 19.6 | 29.7 | 40.1 | 50.6 | 60.2 | 69.4 | 79.0 | 90.7 | 100.7 |
| average titer | 4.4 | 4.3 | 4.5 | 4.6 | 4.2 | 4.5 | 4.5 | N/A | 4.6 | 4.4 |

The results indicate that the sonication did not impact the live titer of the product in any measurable manner.

Virus Split Ratio

The virus split ratio (VSR) can be calculated by comparing the amount of virus particles (as measured by live titer) used to infect a culture to the amount of virus particles that is outputted by the same culture.

Knowing the live titer of the seed used to infect the culture (Ts), the volume of seed used to infect the culture (Vs), the volume of culture (Vc) and the titer of the culture (Tc) the virus split ratio can be calculated as follow:

$$VSR = \frac{Vc \times 10^{Tc}}{Vs \times 10^{Ts}}$$

Figure 6:
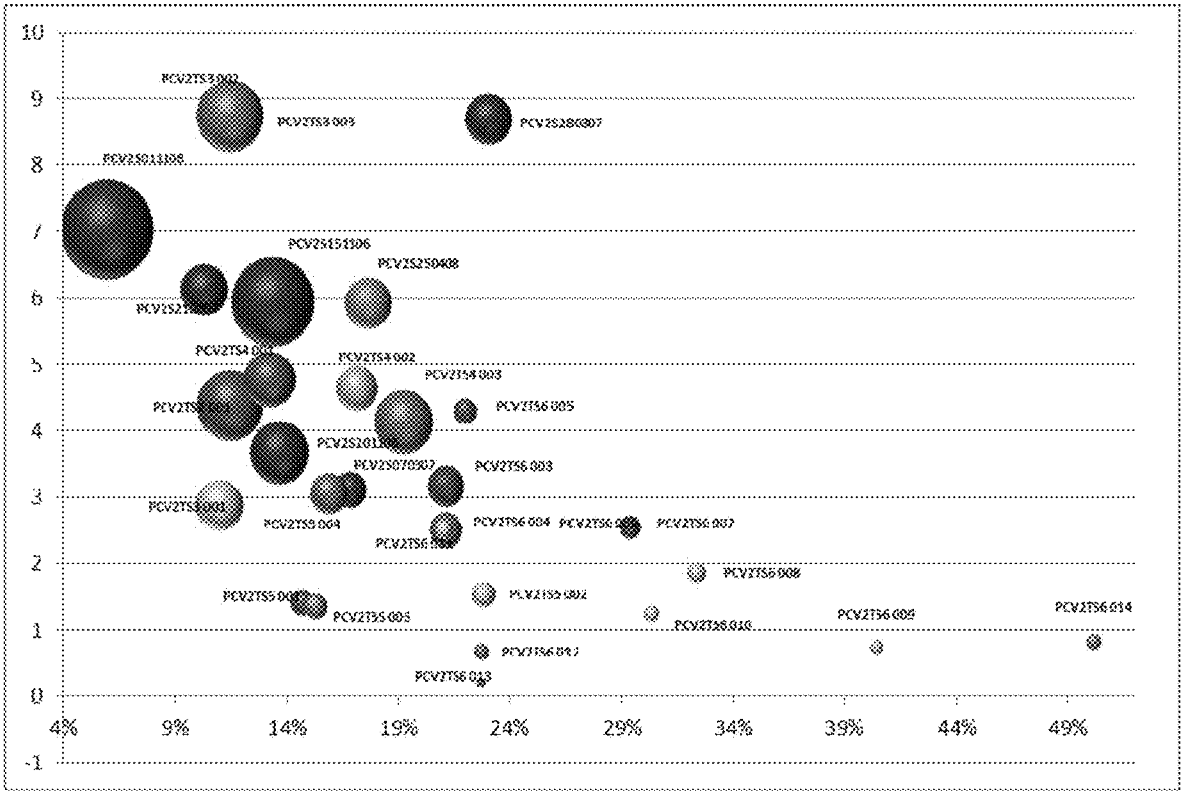
FIG. 6 illustrates the VSR function of the percentage of seed percentage per volume of culture.
Figure 8C:
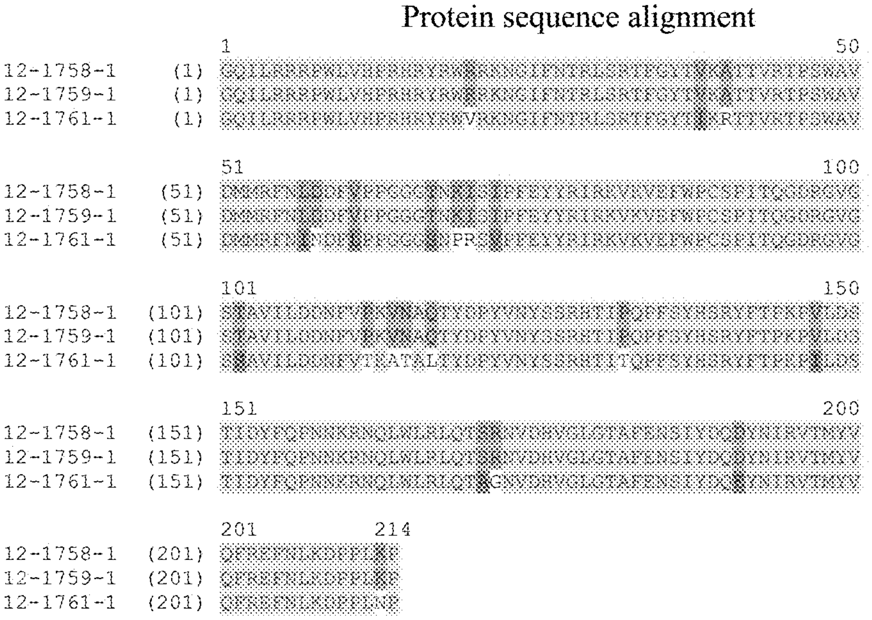

The chart in FIG. 6 trends the VSR function of the percentage of seed volume (lx) and the live titer of the seed produced (size of the bubbles). This chart shows the impact of the inoculation rate on the VSR which, in return, impacts the titer of the seed produced. The persistently infected cell line method is able to maintain a VSR of about 6 which the current process cannot.

The split ratio of 6 could be used in the scale up as shown in Table 6 below. However, any ratio in the range from 4-9 may be used.

TABLE 6

| passage | volume (L) | technology |
|---|---|---|
| X + 4 | 1.2 | RB |
| X + 5 | 6 | RB |
| X + 6 | 36 | RB |
| X + 7 | 150 | reactor |
| AI | 800 | reactor |

In this case, a full scale up would look as follow:

- X+1 production at 1.2 L in RB→trypsinization
- X+2 production using the entirety of the X+1 at 7.2 L in RB→trypsinization
- X+3 production using the entirety of the X+2 at 43.2 L in RB→trypsinization, sonication, freezing and storage
- X+4 production using part of the frozen X+3 at 1.2 L→trypsinization
- X+5 production using the entirety of the X+4 at 6 L in RB→trypsinization
- X+6 production using the entirety of the X+5 at 36 L in RB→trypsinization
- X+7 production using the entirety of the X+6 at 150 L in reactor→trypsinization
- AI production using the entirety of the X+7 at 800 L in reactor.

Example 3 Live Titer and ELISA Titer Determination

Live Titer—Titration and Identity by Indirect Immonufluorescence of PCV2 Virus in PK15 Cells Two- to four-day old PK15 cells were used to prepare a cell suspension of 120,000 cells/ml using DMEM media with 5% FBS, 20 mM glucosamine as the diluent. PCV2 samples were serially diluted with DMEM+5% FBS. 100 ul of diluted PCV2 samples and 100 ul of PK15 cell suspension were added to the wells of a 96-well plate. The plate was incubated at 37±1° C. $CO_2$ for 4 days and rinsed with 100 μl/well PBS. Acetone fixation of the plate was done by adding 100 μl/well of 90% acetone and placing the plate in a −15° C. to −25° C. freezer for 30 minutes. The acetone was then decanted and the plate was air dried completely.

The monoclonal antibody to PCV2 was diluted 1:200 in PBS and 100 μl/well of the diluted monoclonal antibody was added to the dried plate. The plate was incubated at 37±1° C. and 4±1 $CO_2$ for 25-35 minutes. The plate was washed twice with 100 μl/well with PBS and 100 μl/well Anti-Mouse IgG conjugate (FITC, produced in rabbit, IgG fraction of antiserum, Sigma F-9137) diluted in PBS 1:50 were added to the plate. The plate was again incubated at 37±1° C. and 4±1 $CO_2$ for 25-35 minutes. The plate was washed once with 100 μl/well with PBS and once with 100 μl/well neutral pH water (50% tap water/50% DI water). The plate was read using a fluorescence microscope. PCV2 infected cells show a specific intranuclear fluorescence. For the calculation of the titer, wells showing at least three fluorescent cells are considered positive. For identification, the well is positive if one or more cells are fluorescent.

The calculation of the titer is carried out by angular transformation or according to Karber's method, for which the formula is:

$$T=d+[r/N]\times[n+N/2]+1$$

T=titer d=dilution with 100% of wells to show a fluorescent focus r=dilution ratio N=number of wells per rate dilution n=number of wells showing a fluorescence for rate dilution above d ELISA Titration of PCV2 Virus ELISA tests were done in 96-well plate. The wells were coated with 120 µl antibody against PCV2 for 16-22 hours at 2-7° C. The wells were washed once with 100 µl of ELISA blot buffer. PCV2 samples were serially diluted with ELISA buffer and added to the wells. The mixtures were incubated at 35-39° C. for 3 hours, and then washed once with wash buffer. 100 µl peroxidase conjugate was added to each well and the plate was incubated at 35-39° C. for 1 hour. The wells were washed three times with wash buffer and 100 µl of peroxidase substrate were added. The mixtures were kept in the dark at 15-30° C. for 30 minutes. The reaction was stopped by adding 50 µl $H_2SO_4$ to the wells. The plate was read at dual wavelengths of 450 nm and 630 nm and ELISA titer is calculated.

Example 4 PCV2 Efficacy Induced by PCV2 Produced in Persistently Infected PK15 Cells Three PCV2 isolates 12-1761-1 (type B), 12-1758-1 (type A), and 12-1759-1 (type A) were selected based on sequence analysis of capsid region (ORF2) and grown on PK15 cells. The production of PCV2 was carried out using the persistently infected PK15 cells. Briefly, the PK15 cells were placed in DMEM medium containing 200 µg/ml dextran sulfate and 1% L glutamine (No FBS) and infection was carried at MOI 0.01-0.1 and incubated at 37° C. for 1 hr. After 1 hr, an equal volume of DMEM containing 10% FBS and 1% L glutamine was added and incubated at 37° C. Once the cells reached 80-90% confluency, they were treated with HyQtase and were split 1:4 into DMEM medium supplemented with 5% FBS+1% L glutamine. The final split after 11-12 passages was carried out in DMEM medium containing 0%, 2% and 5% serum.

After the final split and the cells achieved 90-95% confluence, the fluids were harvested using HyQtase and the individual isolates were pooled to a final volume of 10 L each. Prior to inactivation a sample was removed to determine the number of viable viral particles present using $TCID_{50}$. The remaining harvest fluids were inactivated using binary ethylenimine (BEI) and processed for formulating final vaccine. Briefly, the PCV2 fluids were treated with Triton 0.1%, and filtered through a 0.2 µm PES filter. Finally, they were concentrated through 100 KDa mPES hollow fiber to yield 10× concentration. The vaccine was stored at 4° C. and formulated with 67% TS6 (U.S. Pat. No. 7,371,395) for the first study and 66% TS6 for the second study.

The chemical inactivation produces enumerable structural changes, including for example, formation of new chemical bonds via chemical crosslinking, irreversible chemical alteration of the nucleic acid and protein coat (Uittenbogaard, 2011, Journal of Biological Chemistry, 286(42): pp 36198-36214; Gard, Bull. Wld Hlth Org., 1957, 17, 979-989).

Sequence analysis of PCV2 isolates used in this study indicated that the two PCV2-ORF2 type A isolates are 99% identical at nucleotide level and 100% identical at amino acid level, the PCV2-ORF2 type B isolate has 99% sequence identity with PCV2-ORF2 type A at both the nucleotide and amino acid levels. The PCV2 type B grows approximately 1 log higher than type A after 12-13 in vitro passages on PK15 cells (See Table 7). PCV2 type B isolate (12-1761-1) was chosen for all animal trials.

TABLE 7

| PCV2 titration results ($TCID_{50}$/mL) | | | | |
|---|---|---|---|---|
| passage | 12-1758-1 | 12-1759-1 | 12-1761-1 | Positive control |
| X + 1 | 2.7 | 2.4 | 3.5 | 2.4 |
| X + 2 | N/A | 2.4 | N/A | N/A |
| X + 3 | 2.4 | 1.9 | 2.4 | 2.9 |
| X + 4 | 2.7 | 3.9 | 5.2 | 3.2 |
| X + 5 | 4.9 | 2.9 | 4.7 | 3.4 |
| X + 6 | 4.2 | 3.4 | 4.4 | 3.4 |
| X + 7 | 4.4 | 3.4 | 4.9 | 3.9 |
| X + 8 | 4.4 | 3.9 | 5.4 | 3.9 |
| X + 9 | 4.9 | 3.9 | 5.4 | 4.2 |
| X + 10 | 5.9 | 4.9 | 6.2 | 4.2 |
| X + 11 | 5.4 | 5.2 | 6.2 | 4.4 |
| X + 12 | 5.2 | 4.9 | 6.2 | 4.9 |

A field trial was carried out to test the PCV2 vaccines. The study was designed to determine the serological response to PCV2 type B isolate (12-1761-1) formulated based on $TCID_{50}$ with TS6 as adjuvant. Forty pigs were enrolled in the study with ten pigs in each group for total of 4 groups. The pigs were approximately 8-9 weeks of age. The pigs were prescreened for PCV2 and only PCV2 negative pigs were used in this study. Pigs were vaccinated with 2 ml vaccine intramuscularly. The study design is summarized in Table 8 below.

TABLE 8

| Study design | | |
|---|---|---|
| Group | Vaccinate/bleed at D0 and D21 | |
| A | control, vaccinate with 67% TS6 + 1XPBS (A) | Final bleed at D35 |
| B | PCV2-5.1 logs per dose | |
| C | PCV2-6.5 logs per dose | |
| D | Circumvet* as directed | |

*Circumvent™ commercial PCV type 2 vaccine, Intervet

All blood samples were sent to two diagnostics laboratory (IS and KS) for PCV2 IFA (Indirect fluorescent-antibody) testing.

Results

When pigs were immunized with either 5.1 or 6.5 logs of PCV2 vaccine, 100% seroconversion was detected on day 21 (see Table 9-12).

TABLE 9

| Serological results of group A<br>Group A: Control, Vaccinated with 67% TS6 + 1xPBS | | | | |
|---|---|---|---|---|
| | D0 | | D21 | |
| Pig ID | KS | IS | KS | IS |
| 216 | 20 | 0 | 640 | 0 |
| 222 | 20 | 0 | 20 | 160 |
| 237 | 20 | 0 | 1280 | 0 |
| 242 | 20 | 0 | 640 | 0 |

TABLE 9-continued

Serological results of group A
Group A: Control, Vaccinated with 67% TS6 + 1xPBS

| | D0 | | D21 | |
|---|---|---|---|---|
| Pig ID | KS | IS | KS | IS |
| 244 | 20 | 0 | 20 | 0 |
| 261 | 20 | 0 | 20 | 0 |
| 269 | 20 | 0 | 20 | 0 |
| 271 | 20 | 0 | 1280 | 0 |
| 272 | 20 | 0 | 20 | 0 |
| 586 | 20 | 0 | 20 | 0 |
| GM: | 20.00 | 0.00 | 91.90 | 0.00 |
| Average: | 20.00 | 0.00 | 396.00 | 16.00 |

KS
<140 = 20
>5120 = 10240
IS
<160 = 0
>=1280 = 1280

TABLE 10

Serological results of group B
Group B: PCV2 - 5.1 logs/dose

| | D0 | | D21 | | D34 | |
|---|---|---|---|---|---|---|
| Pig ID | KS | IS | KS | IS | KS | IS |
| 50 | 20 | 0 | 10240 | 1280 | 10240 | 1280 |
| 213 | 20 | 0 | 10240 | 1280 | 10240 | 1280 |
| 225 | 20 | 0 | 10240 | 1280 | 10240 | 1280 |
| 226 | 20 | 0 | 10240 | 160 | 160 | 320 |
| 232 | 20 | 0 | 10240 | 640 | 10240 | 640 |
| 240 | 20 | 0 | 10240 | 1280 | 10240 | 1280 |
| 241 | 20 | 0 | 10240 | 1280 | 10240 | 1280 |
| 249 | 20 | 0 | 10240 | 320 | 10240 | 320 |
| 253 | 20 | 0 | 10240 | 320 | 160 | 0 |
| 268 | 20 | 0 | 10240 | 1280 | 10240 | 1280 |
| GM: | 20.00 | 0.00 | 10240.00 | 735.17 | 4457.22 | 221.81 |
| Average: | 20.00 | 0.00 | 10240.00 | 912.00 | 8224.00 | 896.00 |

TABLE 11

Serological results of group C
Group C: PCV2 - 6.5 logs/dose

| | D0 | | D21 | | D34 | |
|---|---|---|---|---|---|---|
| Pig ID | KS | IS | KS | IS | KS | IS |
| 212 | 20 | 0 | 10240 | 1280 | 10240 | 1280 |
| 233 | 20 | 0 | 10240 | 640 | 10240 | 1280 |
| 236 | 20 | 0 | 10240 | 1280 | 20 | 640 |
| 262 | 20 | 0 | 10240 | 1280 | 10240 | 1280 |
| 264 | 20 | 0 | 10240 | 640 | Euth | Euth |
| 266 | 20 | 0 | 10240 | 1280 | 10240 | 1280 |

TABLE 11-continued

Serological results of group C
Group C: PCV2 - 6.5 logs/dose

| | D0 | | D21 | | D34 | |
|---|---|---|---|---|---|---|
| Pig ID | KS | IS | KS | IS | KS | IS |
| 270 | 20 | 0 | 10240 | 1280 | 10240 | 1280 |
| 273 | 20 | 0 | 10240 | 1280 | 10240 | 1280 |
| 286 | 20 | 0 | 10240 | 1280 | 10240 | 1280 |
| 292 | 20 | 0 | 10240 | 640 | 640 | 160 |
| GM: | 20.00 | 0.00 | 10240.00 | 1039.68 | 3762.52 | 940.63 |
| Average: | 20.00 | 0.00 | 10240.00 | 1088.00 | 8037.78 | 1084.44 |

Euth = Euthanized

TABLE 12

Serological results of group D
Group D: Circumvent (2 ml IM - as directed)

| | D0 | | D21 | | D34 | |
|---|---|---|---|---|---|---|
| Pig ID | KS | IS | KS | IS | KS | IS |
| 209 | 20 | 0 | 10240 | 640 | 10240 | 1280 |
| 214 | 20 | 0 | 10240 | 320 | 10240 | 1280 |
| 229 | 20 | 0 | 10240 | 640 | 10240 | 1280 |
| 239 | 20 | 0 | 10240 | 320 | 10240 | 1280 |
| 257 | 20 | 0 | 10240 | 640 | 10240 | 1280 |
| 259 | 20 | 0 | 10240 | 640 | 10240 | 1280 |
| 260 | 20 | 0 | 10240 | 640 | 10240 | 1280 |
| 274 | 20 | QNS | 10240 | 160 | 10240 | 1280 |
| 287 | 20 | 0 | 10240 | 320 | 10240 | 1280 |
| 580 | 20 | 0 | 10240 | 640 | 10240 | 1280 |
| GM: | 20.00 | 0.00 | 10240.00 | 452.55 | 10240.00 | 1280.00 |
| Average: | 20.00 | 0.00 | 10240.00 | 496.00 | 10240.00 | 1280.00 |

***

Having thus described in detail preferred embodiments of the present invention, it is to be understood that the invention defined by the appended claims is not to be limited by particular details set forth in the above description as many apparent variations thereof are possible without departing from the spirit or scope thereof.

All documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention

What is claimed is:

1. An inactivated PCV2 vaccine prepared by a method comprising the steps of (1) preparing PK15 (porcine kidney) cells for infection; (2) infecting the PK15 cells with PCV2; (3) culturing and expanding the infected PK15 cells through passages, and (4) isolating or harvesting PCV2, wherein the PCV2 was inactivated by a physical inactivation method comprising subjecting the virus to energy-rich radiation selected from a group comprising UV light, X-radiation, and gamma-radiation, and wherein the PCV2 comprises a polynucleotide encoding a PCV2 ORF2 according to SEQ ID NO:2, 4, or 6.

2. The inactivated PCV2 vaccine of claim 1, wherein the infection of PCV2 is carried out in the absence of glucosamine.

3. The inactivated PCV2 vaccine of claim 1, wherein the PK15 cells are trypsinized at the end of each passage.

4. The inactivated PCV2 vaccine of claim 1, wherein the PK15 infected cells are incubated at 36±2° C.

5. The inactivated PCV2 vaccine of claim 1, wherein the incubation period for viral growth ranges from 2-8 days.

6. The inactivated PCV2 vaccine of claim 1, wherein the passages range from 2-10 passages.

7. The inactivated PCV2 vaccine of claim 1, wherein the passages beyond the initial cell passage/infection are carried out without the addition of fresh PK15 cells.

8. The inactivated PCV2 vaccine of claim 1, wherein the virus split ratio (VSR) used for the passages ranges from 4-9.

9. The inactivated PCV2 vaccine of claim 1, wherein the PCV2 is harvested from the culture by sonication and subsequent removing of the resultant cell debris by centrifugation.

10. The inactivated PCV2 vaccine of claim 1, wherein the vaccine further comprises one or more swine pathogens or viruses.

11. The inactivated PCV2 vaccine of claim 1, wherein the polynucleotide according to SEQ ID NO:1, 3, or 5.

12. The inactivated PCV2 vaccine of claim 1, further comprises a pharmaceutically or veterinarily acceptable carriers, excipients, adjuvants, or stabilizers.

* * * * *

SEQUENCE LISTING

```
<160> NUMBER OF SEQ ID NOS: 6

<210> SEQ ID NO 1
<211> LENGTH: 645
<212> TYPE: DNA
<213> ORGANISM: artificial
<220> FEATURE:
<223> OTHER INFORMATION: DNA sequence of PCV2 isolate 12-1761-1

<400> SEQUENCE: 1
```

-continued

```
ggccagatcc tccgccgccg cccctggctc gtccaccccc gccaccgtta ccgctgggta     60

aggaaaaatg gcatcttcaa cacccgccta tcccgcacct tcggatatac tatcaagcga    120

accacagtca gaacgccctc ctgggcggtg gacatgatga gattcaatat taatgacttt    180

cttcccccag gagggggctc aaacccccgc tctgtgccct ttgaatacta cagaataaga    240

aaggttaagg ttgaattctg gccctgctcc ccgatcaccc agggtgacag gggagtgggc    300

tccagtgctg ttattctaga tgataacttt gtaacaaagg ccacagccct cacctatgac    360

ccctatgtaa actactcctc ccgccatacc ataacccagc ccttctccta ccactcccgc    420

tacttcaccc ccaaacctat cctagattcc actattgatt acttccaacc aaacaacaaa    480

agaaaccagc tgtggctaag actacaaact gctggaaatg tagaccacgt aggcctcggc    540

actgcattcg aaaacagtat atacgaccag gaatacaata tccgtgtaac catgtatgta    600

caattcagag aatttaatct taaagacccc ccacttaacc cttaa                    645
```

<210> SEQ ID NO 2
<211> LENGTH: 214
<212> TYPE: PRT
<213> ORGANISM: artificial
<220> FEATURE:
<223> OTHER INFORMATION: Protein sequence of PCV2 isolate 12-1761-1

<400> SEQUENCE: 2

```
Gly Gln Ile Leu Arg Arg Arg Pro Trp Leu Val His Pro Arg His Arg
1               5                   10                  15

Tyr Arg Trp Val Arg Lys Asn Gly Ile Phe Asn Thr Arg Leu Ser Arg
            20                  25                  30

Thr Phe Gly Tyr Thr Ile Lys Arg Thr Thr Val Arg Thr Pro Ser Trp
        35                  40                  45

Ala Val Asp Met Met Arg Phe Asn Ile Asn Asp Phe Leu Pro Pro Gly
    50                  55                  60

Gly Gly Ser Asn Pro Arg Ser Val Pro Phe Glu Tyr Tyr Arg Ile Arg
65                  70                  75                  80

Lys Val Lys Val Glu Phe Trp Pro Cys Ser Pro Ile Thr Gln Gly Asp
                85                  90                  95

Arg Gly Val Gly Ser Ser Ala Val Ile Leu Asp Asp Asn Phe Val Thr
            100                 105                 110

Lys Ala Thr Ala Leu Thr Tyr Asp Pro Tyr Val Asn Tyr Ser Ser Arg
        115                 120                 125

His Thr Ile Thr Gln Pro Phe Ser Tyr His Ser Arg Tyr Phe Thr Pro
    130                 135                 140

Lys Pro Ile Leu Asp Ser Thr Ile Asp Tyr Phe Gln Pro Asn Asn Lys
145                 150                 155                 160

Arg Asn Gln Leu Trp Leu Arg Leu Gln Thr Ala Gly Asn Val Asp His
                165                 170                 175

Val Gly Leu Gly Thr Ala Phe Glu Asn Ser Ile Tyr Asp Gln Glu Tyr
            180                 185                 190

Asn Ile Arg Val Thr Met Tyr Val Gln Phe Arg Glu Phe Asn Leu Lys
        195                 200                 205

Asp Pro Pro Leu Asn Pro
    210
```

<210> SEQ ID NO 3
<211> LENGTH: 645
<212> TYPE: DNA

```
<213> ORGANISM: artificial
<220> FEATURE:
<223> OTHER INFORMATION: DNA sequence of PCV2 isolate 12-1758-1

<400> SEQUENCE: 3

ggccaaatcc tccgccgccg cccctggctc gtccaccccc gccaccgcta ccgatggaga     60

aggaaaaatg gcatcttcaa cacccgcctc tcccgcacct tcggatatac tgtcaaggct    120

accacagtca gaacgccctc ctgggcggtg gacatgatga gatttaatct tgacgacttt    180

gttcccccgg gagggggac caacaaaatc tctataccct ttgaatacta cagaataaga     240

aaagttaagg ttgaattctg gccctgctcc cccatcaccc agggtgatag gggagtgggc    300

tccactgctg ttattctaga tgataacttt gtaccaaagg tcaatgccca aacctatgac    360

ccatatgtaa actactcctc ccgccataca atcccccaac ccttctcgta ccactcccgt    420

tacttcacac ccaaacctgt tcttgactcc actattgatt acttccaacc aaataacaaa    480

aggaatcagc tttggctgag gctacaaacc tctagaaatg tggaccacgt aggcctcggc    540

actgcgttcg aaaacagtat atacgaccag gactacaata tccgtgtaac catgtatgta    600

caattcagag aatttaatct taaagacccc ccacttaaac cctaa                   645


<210> SEQ ID NO 4
<211> LENGTH: 214
<212> TYPE: PRT
<213> ORGANISM: artificial
<220> FEATURE:
<223> OTHER INFORMATION: Protein sequence of PCV2 isolate 12-1758-1

<400> SEQUENCE: 4

Gly Gln Ile Leu Arg Arg Arg Pro Trp Leu Val His Pro Arg His Arg
1               5                   10                  15

Tyr Arg Trp Arg Arg Lys Asn Gly Ile Phe Asn Thr Arg Leu Ser Arg
            20                  25                  30

Thr Phe Gly Tyr Thr Val Lys Ala Thr Thr Val Arg Thr Pro Ser Trp
        35                  40                  45

Ala Val Asp Met Met Arg Phe Asn Leu Asp Asp Phe Val Pro Pro Gly
    50                  55                  60

Gly Gly Thr Asn Lys Ile Ser Ile Pro Phe Glu Tyr Tyr Arg Ile Arg
65                  70                  75                  80

Lys Val Lys Val Glu Phe Trp Pro Cys Ser Pro Ile Thr Gln Gly Asp
                85                  90                  95

Arg Gly Val Gly Ser Thr Ala Val Ile Leu Asp Asp Asn Phe Val Pro
            100                 105                 110

Lys Val Asn Ala Gln Thr Tyr Asp Pro Tyr Val Asn Tyr Ser Ser Arg
        115                 120                 125

His Thr Ile Pro Gln Pro Phe Ser Tyr His Ser Arg Tyr Phe Thr Pro
    130                 135                 140

Lys Pro Val Leu Asp Ser Thr Ile Asp Tyr Phe Gln Pro Asn Asn Lys
145                 150                 155                 160

Arg Asn Gln Leu Trp Leu Arg Leu Gln Thr Ser Arg Asn Val Asp His
                165                 170                 175

Val Gly Leu Gly Thr Ala Phe Glu Asn Ser Ile Tyr Asp Gln Asp Tyr
            180                 185                 190

Asn Ile Arg Val Thr Met Tyr Val Gln Phe Arg Glu Phe Asn Leu Lys
        195                 200                 205

Asp Pro Pro Leu Lys Pro
    210
```

<210> SEQ ID NO 5
<211> LENGTH: 645
<212> TYPE: DNA
<213> ORGANISM: artificial
<220> FEATURE:
<223> OTHER INFORMATION: DNA sequence of PCV2 isolate 12-1759-1

<400> SEQUENCE: 5

```
ggccagatcc tccgccgccg cccctggctc gttcaccccc gccaccgcta ccgttggaga     60

aggaaaaatg gcatcttcaa cacccgcctc tcccgcacct tcggatatac tgtcaaggct    120

accacagtca gaacgccctc ctgggcggtg gacatgatga gatttaatct tgacgacttt    180

gttcccccgg gagggggac caacaaaatc tctataccct ttgaatacta cagaataaga    240

aaagttaagg ttgaattctg gccctgctcc cccatcaccc agggtgatag gggagtgggc    300

tccactgctg ttattctaga tgataacttt gtaccaaagg tcaatgccca aacctatgac    360

ccatatgtaa actactcctc ccgccataca atcccccaac ccttctccta ccactcccgt    420

tacttcacac ccaaacctgt tcttgactcc actattgatt acttccaacc aaataacaaa    480

aggaatcagc tttggctgag gctacaaacc tctagaaatg tggaccacgt aggcctcggc    540

actgcgttcg aaaacagtat atacgaccag gactacaata tccgtgtaac catgtatgta    600

caattcagag aatttaatct taaagacccc ccacttaaac cctaa                    645
```

<210> SEQ ID NO 6
<211> LENGTH: 214
<212> TYPE: PRT
<213> ORGANISM: artificial
<220> FEATURE:
<223> OTHER INFORMATION: Protein sequence of PCV2 isolate 12-1759-1

<400> SEQUENCE: 6

```
Gly Gln Ile Leu Arg Arg Arg Pro Trp Leu Val His Pro Arg His Arg
1               5                   10                  15

Tyr Arg Trp Arg Arg Lys Asn Gly Ile Phe Asn Thr Arg Leu Ser Arg
            20                  25                  30

Thr Phe Gly Tyr Thr Val Lys Ala Thr Thr Val Arg Thr Pro Ser Trp
        35                  40                  45

Ala Val Asp Met Met Arg Phe Asn Leu Asp Asp Phe Val Pro Pro Gly
    50                  55                  60

Gly Gly Thr Asn Lys Ile Ser Ile Pro Phe Glu Tyr Tyr Arg Ile Arg
65                  70                  75                  80

Lys Val Lys Val Glu Phe Trp Pro Cys Ser Pro Ile Thr Gln Gly Asp
                85                  90                  95

Arg Gly Val Gly Ser Thr Ala Val Ile Leu Asp Asp Asn Phe Val Pro
            100                 105                 110

Lys Val Asn Ala Gln Thr Tyr Asp Pro Tyr Val Asn Tyr Ser Ser Arg
        115                 120                 125

His Thr Ile Pro Gln Pro Phe Ser Tyr His Ser Arg Tyr Phe Thr Pro
    130                 135                 140

Lys Pro Val Leu Asp Ser Thr Ile Asp Tyr Phe Gln Pro Asn Asn Lys
145                 150                 155                 160

Arg Asn Gln Leu Trp Leu Arg Leu Gln Thr Ser Arg Asn Val Asp His
                165                 170                 175

Val Gly Leu Gly Thr Ala Phe Glu Asn Ser Ile Tyr Asp Gln Asp Tyr
            180                 185                 190
```

-continued

```
Asn Ile Arg Val Thr Met Tyr Val Gln Phe Arg Glu Phe Asn Leu Lys
        195                 200                 205

Asp Pro Pro Leu Lys Pro
    210
```